(12) United States Patent
Makower et al.

(10) Patent No.: US 10,660,995 B2
(45) Date of Patent: *May 26, 2020

(54) BREAST PUMP SYSTEM AND METHODS

(71) Applicant: EXPLORAMED NC7, INC., Mountain View, CA (US)

(72) Inventors: Joshua Makower, Los Altos Hills, CA (US); John Y Chang, Los Altos, CA (US); Brendan M Donohoe, Fairfax, CA (US); Michael Landry, Austin, TX (US); Michele Torosis, Los Altos, CA (US)

(73) Assignee: ExploraMed NC7, Inc., Mountain View, CA (US)

( * ) Notice: Subject to any disclaimer, the term of this patent is extended or adjusted under 35 U.S.C. 154(b) by 458 days.

This patent is subject to a terminal disclaimer.

(21) Appl. No.: 15/361,974

(22) Filed: Nov. 28, 2016

(65) Prior Publication Data

US 2017/0080134 A1 Mar. 23, 2017

Related U.S. Application Data

(63) Continuation-in-part of application No. PCT/US2015/041271, filed on Jul. 21, 2015.
(Continued)

(51) Int. Cl.
*A61M 1/00* (2006.01)
*A61M 1/06* (2006.01)
(Continued)

(52) U.S. Cl.
CPC ............ *A61M 1/06* (2013.01); *A61M 1/0066* (2013.01); *A61M 1/1039* (2014.02);
(Continued)

(58) Field of Classification Search
CPC .......... A61M 1/007; A61M 2210/1007; A61M 1/1039; A61M 1/1041; A61M 5/14228;
(Continued)

(56) References Cited

U.S. PATENT DOCUMENTS 4,263,912 A 4/1981 Adams
4,311,141 A * 1/1982 Diamond ................ A61M 1/06
604/74

(Continued)

FOREIGN PATENT DOCUMENTS

CN 2628060 Y 7/2004
EP 2456482 B1 11/2016
(Continued)

OTHER PUBLICATIONS

Chiu et al., Development of a piezoelectric polyvinylidene fluoride (PVDF) polymer based sensor patch for simultaneous heartbeat and respiration monitoring, Sensors and Actuators A: Physical, vol. 189, Jan. 15, 2013, pp. 328-334.
(Continued)

*Primary Examiner* — Bhisma Mehta
*Assistant Examiner* — William R Frehe

(57) ABSTRACT

Systems and methods for pumping milk from a breast, wherein the milk is expressed from the breast under suction and milk is expulsed from the pumping mechanism to a collection container under positive pressure.

14 Claims, 14 Drawing Sheets

Related U.S. Application Data

(60) Provisional application No. 62/050,810, filed on Sep. 16, 2014, provisional application No. 62/027,685, filed on Jul. 22, 2014.

(51) Int. Cl.
*A61M 1/10* (2006.01)
*A61M 5/142* (2006.01)
*A61B 18/00* (2006.01)

(52) U.S. Cl.
CPC .............. *A61B 2018/00333* (2013.01); *A61M 5/14228* (2013.01); *A61M 2205/3331* (2013.01); *A61M 2210/1007* (2013.01)

(58) Field of Classification Search
CPC ....................... A61B 2018/00333; A61J 13/00; F04B 43/08; F04B 43/082; F04B 43/09; F04B 49/065
See application file for complete search history.

(56) References Cited

U.S. PATENT DOCUMENTS

| | | | |
|---|---|---|---|
| 5,542,921 A | 8/1996 | Meyers et al. | |
| 5,634,468 A | 6/1997 | Platt et al. | |
| 5,658,133 A * | 8/1997 | Anderson | A61M 5/172 417/63 |
| 5,827,191 A | 10/1998 | Rosenfeld | |
| 6,273,868 B1 | 8/2001 | Nordvik | |
| 6,287,252 B1 | 9/2001 | Lugo | |
| 6,328,082 B1 | 12/2001 | Lafond | |
| D459,233 S | 6/2002 | Young | |
| 6,440,100 B1 | 8/2002 | Prentiss | |
| 6,547,756 B1 | 4/2003 | Greter et al. | |
| 6,579,258 B1 | 6/2003 | Atkin et al. | |
| 6,712,785 B2 | 3/2004 | Morton et al. | |
| 7,201,735 B2 | 4/2007 | Atkin et al. | |
| 7,223,255 B2 | 5/2007 | Myers et al. | |
| 7,621,797 B1 | 11/2009 | Hershkovich | |
| 7,824,363 B2 | 11/2010 | Myers | |
| 7,988,661 B2 | 8/2011 | Silver et al. | |
| 8,057,425 B1 | 11/2011 | Myers et al. | |
| 8,070,715 B2 | 12/2011 | Quackenbush et al. | |
| 8,070,716 B2 | 12/2011 | Sutrina et al. | |
| 8,262,606 B2 | 9/2012 | Greter et al. | |
| 8,282,596 B2 | 10/2012 | Greter et al. | |
| 8,353,865 B2 | 1/2013 | Thilwind et al. | |
| 8,376,986 B2 | 2/2013 | Van Schijndel et al. | |
| 8,671,701 B2 | 3/2014 | McKendry | |
| 8,684,961 B2 | 4/2014 | Gottenbos et al. | |
| 8,801,495 B1 | 8/2014 | Guindon | |
| 9,050,404 B2 | 6/2015 | Silver et al. | |
| 9,162,016 B2 | 10/2015 | Geddes | |
| 9,173,587 B2 | 11/2015 | Van Schijndel et al. | |
| 9,199,017 B2 | 12/2015 | Greter | |
| 9,278,167 B2 | 3/2016 | Aalders et al. | |
| 1,197,011 A1 | 9/2016 | Cilino | |
| 9,683,562 B2 * | 6/2017 | Davis | A61M 39/08 |
| 2003/0191433 A1 | 10/2003 | Prentiss | |
| 2004/0024351 A1 | 2/2004 | Greter et al. | |
| 2004/0101414 A1 * | 5/2004 | Gharib | F04B 43/08 417/53 |
| 2004/0127845 A1 | 7/2004 | Renz et al. | |
| 2005/0059928 A1 | 3/2005 | Larsson | |
| 2005/0131332 A1 | 6/2005 | Kelly et al. | |
| 2005/0234370 A1 | 10/2005 | Beal et al. | |
| 2006/0106334 A1 | 5/2006 | Jordan et al. | |
| 2008/0045888 A1 | 2/2008 | Edwards et al. | |
| 2008/0177224 A1 | 7/2008 | Kelly et al. | |
| 2008/0243059 A1 | 10/2008 | Yamashita et al. | |
| 2009/0024080 A1 | 1/2009 | Rohrig | |
| 2010/0217148 A1 | 8/2010 | Binder | |
| 2011/0071466 A1 | 3/2011 | Silver et al. | |
| 2011/0196291 A1 | 8/2011 | Vischer et al. | |
| 2011/0245763 A1 | 10/2011 | Myers | |
| 2012/0101575 A1 | 4/2012 | Horne et al. | |
| 2012/0277636 A1 | 11/2012 | Blondheim et al. | |
| 2012/0277728 A1 * | 11/2012 | Weber | A61M 1/064 604/514 |
| 2013/0023821 A1 * | 1/2013 | Khalil | A61M 1/064 604/74 |
| 2013/0123688 A1 | 5/2013 | Bosman et al. | |
| 2013/0131588 A1 | 5/2013 | Silver et al. | |
| 2013/0177455 A1 | 7/2013 | Kamen et al. | |
| 2014/0066734 A1 | 3/2014 | Zdeblick | |
| 2015/0100016 A1 | 4/2015 | Liao | |
| 2015/0292500 A1 | 10/2015 | Girard et al. | |
| 2016/0000980 A1 * | 1/2016 | Alvarez | A61M 1/06 604/514 |
| 2016/0256618 A1 * | 9/2016 | Embleton | A61M 1/068 |

FOREIGN PATENT DOCUMENTS

| | | |
|---|---|---|
| EP | 3151876 B1 | 11/2017 |
| GB | 2342446 A | 4/2000 |
| JP | 2005279044 | 10/2005 |
| RU | 2012 107356 | 5/2012 |
| WO | WO 2000/57934 | 10/2000 |
| WO | WO2001054488 | 8/2001 |
| WO | WO2011010255 | 1/2011 |
| WO | WO2011144984 A | 11/2011 |
| WO | WO2012037848 | 3/2012 |
| WO | WO 2013076055 | 5/2013 |
| WO | WO2013088310 | 6/2013 |
| WO | WO 2013/187763 | 12/2013 |
| WO | WO2013184004 | 12/2013 |
| WO | WO2015120321 | 8/2015 |

OTHER PUBLICATIONS

Double Electric Breast Pump/Dr. Brown's, http://www.drbrownsbaby.com/breastfeeding-product/breast-pumps/double-electric, May 15, 2014.

* cited by examiner

BREAST PUMP SYSTEM AND METHODS

FIELD OF THE DISCLOSURE

The present disclosure generally relates to portable, energy efficient breast pump systems and methods for collecting milk from a breast of a nursing mother.

BACKGROUND OF THE DISCLOSURE

As more women become aware that breastfeeding is the best source of nutrition for a baby, and also offers health benefits to the nursing mother, the need is increasing for breast pump solutions that are user-friendly, quiet, discrete and versatile for use by a nursing mother in various situations. This is particularly true for the working mother, who is away from the home for eight to ten hours or more and needs to pump breast milk in order to have it available for her baby, but it is also a requirement for many other situations where the mother is away from the privacy of the home for an extended period, such as during shopping, going out to dinner or other activities.

Although a variety of breast pumps are available, most are awkward and cumbersome, requiring many parts and assemblies and being difficult to transport. Hand pump varieties that are manually driven are onerous to use and can be painful to use. Some powered breast pumps require an AC power source to plug into during use. Some systems are battery driven, but draw down the battery power fairly rapidly as the motorized pump continuously operates to maintain suction during the milk extraction process. Many of the breast pumps available are clearly visible to an observer when the mother is using it, and many also expose the breast of the mother during use.

There is a continuing need for a small, portable, self-powered, energy efficient, wearable breast pump system that is easy to use and is discrete by not exposing the breast of the user and being invisible or nearly unnoticeable when worn.

SUMMARY OF THE DISCLOSURE

Briefly and in general terms, the present disclosure is directed towards breast pump systems and methods. The system can include breast contacting structure and a storage container, and structure configured to deliver extracted milk from a breast to the storage container. A method can involve extracting milk from a breast and pumping the milk to a storage container.

According to one aspect of the present disclosure, a system for pumping milk from a breast can included a skin contact member configured and dimensioned to form a seal with the breast, a conduit in fluid communication with said skin contact member, a driving mechanism configured to compress a region of the conduit, and a valve configured and dimensioned to alternatively seal and release a seal of the conduit at a first location of the conduit between the skin contact member and a second location of the conduit aligned for compression by the driving mechanism. The system can further include a storage container for storing the milk pumped from the breast, the storage container configured for fluid communication with the conduit.

In at least one embodiment, the system further includes a one-way valve in fluid communication with a distal end portion of the conduit or a one-way valve between the storage container and conduit, the one-way valve preventing backflow of milk into the conduit. The one-way valve can be configured to prevent backflow of air into the conduit and can additionally or alternatively have an opening pressure threshold of about 25 mm Hg.

A driving mechanism can be provided and configured to retract away from the conduit, and wherein a suction created by compressing the conduit and allowing the conduit to rebound is a driving force for extracting milk from the breast. The driving mechanism can include a paddle configured to compress the portion of the conduit, and a motor configured to drive the paddle towards and away from the conduit.

In at least one embodiment, a valve can be provided and configured as a compression member and a motor can be configured to drive the compression member toward and away from the conduit. In at least one embodiment, the valve when sealing off the conduit maintains a constant pressure level in a vacuum space between the valve and the breast. Moreover, in certain approaches the driving mechanism and the valve can be configured for coordinated compression and release of compression of the conduit at first and second locations to generate a suction level sufficient to extract milk from the breast. Additionally, the driving mechanism and the valve can be further configured for coordinated movements to create a positive pressure to drive the milk extracted from the breast, through the conduit, away from the breast and pumping mechanism, while maintaining a negative pressure applied to the breast. In at least one embodiment, pressure is sufficient to pump the milk against gravity.

In at least one embodiment, the system further can additionally or alternatively include a controller electrically connected to the pumping mechanism and the valve and configured to control movements of the pumping mechanism and the valve. A battery can be provided and electrically connected to the pumping mechanism and the valve and configured to supply power for movements of the driving mechanism and the valve. The battery can be further electrically connected to the controller, the pumping mechanism and the valve and configured to supply power for operation of the controller and movements of the driving mechanism and the valve.

In one particular approach, the system further includes a pressure sensor located and configured to sense pressure in a space between the skin contact member and the breast when the skin contact member is sealed to the breast. The pressure sensor can also be placed and configured to sense pressure in a space between the skin contact member and the breast, when the skin contact member is sealed to the breast, wherein the pressure sensor is in electronic communication with the controller.

The controller can be configured to adaptively control movements of the pumping mechanism and the valve with input from a feedback loop established with the pressure sensor. Further, in certain approaches, the controller is programmable to change control settings for controlling movements of the pumping mechanism and the valve. The controller can alternatively or additionally be configured to adaptively control movements of the pumping mechanism and the valve based upon real time feedback.

In at least one embodiment, the conduit is designed and configured to resiliently generate a suction less than −60 mm Hg, when resiliently returning from a biased, compressed state toward an unbiased, uncompressed state, when the conduit is connected to the skin contact member and the skin contact member is sealed to the breast. In certain embodiments, the conduit at a first location has a first inside diameter and the conduit at the second location has a second inside diameter, and wherein the second inside diameter is greater than the first inside diameter. In various approaches, a first inside diameter is a first dimension within the range of about 0.040" to about 0.35" mm, and the second inside diameter is a second dimension in the range of about 0.125" to about 1.0". The first dimension can also be within the range of about 0.08" to about 0.20" and the second dimension can be within the range of about 0.25" to about 0.75", or the first dimension is about 0.104" and the second dimension is about 0.375".

In at least one embodiment, the conduit at a first location has a first outside diameter and the conduit at the second location has a second outside diameter, and wherein the second outside diameter is greater than the first outside diameter. The first outside diameter can have a first dimension within the range of about 0.052" mm to about 0.446", and the second outside diameter is a second dimension in the range of about 0.187" to about 1.312", or the first dimension can be within the range of about 0.148" to about 0.37" and the second dimension can be within the range of about 0.375" to about 0.984", or the first dimension is about 0.192" and the second dimension is about 0.563".

Further, the conduit at a first location can have a first wall thickness and the conduit at the second location can have a second wall thickness, and wherein the second wall thickness is greater than the first wall thickness. The first wall thickness is a first dimension within the range of about 0.006" to about 0.055", and the second wall thickness is a second dimension in the range of about 0.020" to about 0.156", or the first dimension is within the range of about 0.013" to about 0.0312" and the second dimension is within the range of about 0.039" to about 0.117". In at least one embodiment, the first dimension is about 0.044" and the second dimension is about 0.094".

In at least one embodiment, the conduit at the first and second locations is compliant and resilient, and wherein portions of the conduit upstream of the first and second locations and downstream of the first and second locations are non-compliant. The system can further include a flange adapter configured to connect the skin contact member and the conduit in fluid communication. The skin contact member can be removably attachable to the flange adapter and further, the driving mechanism and valve can be contained in a housing, and the skin contact member and conduit are removably attachable to the housing.

In additional or alternative various other aspects, the controller is programmed with instructions for a plurality of pumping modes and the controller comprises a selector for manually selecting any one of the plurality of pumping modes. The controller can also include a speed selector adapted for manually modifying a pumping speed of the system, or additionally or alternatively, the controller can include a pumping force selector operable to manually adjust a maximum suction level achieved by the system during pumping.

A breast flange can additionally or alternatively provided and configured and dimensioned to form a seal with the breast. In one approach, the system can include the flange as well as a conduit in fluid communication with the breast flange, the conduit having a capacity to contain a volume, a first compression member configured to compress a first region of the conduit; and a second compression member configured to compress a second region of the conduit, wherein the second compression member is configured to displace a predetermined percentage of the volume upon fully compressing the second region, and wherein the first compression member is configured to displace less than five percent of the predetermined volume upon fully compressing the first region. The first compression member can be configured to displace two percent or less of the predetermined volume upon fully compressing the first region. Also, the first region of the conduit can alternatively or additionally include a first internal space having a first volume and the second region of the conduit comprises a second internal space having a second volume, wherein the second volume is greater than the first volume.

In at least one embodiment, the first region of the conduit comprise a first cross-sectional area and the second region of the conduit comprises a second cross-sectional area, wherein the second cross-sectional area is greater than the first cross-sectional area. The first region of the conduit can be tubular and the second region of the conduit can be tubular, the first region having a first inside diameter and the second region having a second inside diameter, wherein the second inside diameter is greater than the first inside diameter.

According to another aspect of the present disclosure, a method of pumping milk from a breast can involve one or more of providing a breast pump system including a conduit, a pinch valve and a compression member, the pinch valve and the driving member being configured to compress first and second regions of the conduit, respectively, forming a seal of the system against the breast to place the conduit in fluid communication with a nipple of the breast, actuating the compression member to establish a suction level sufficient to extract milk from the breast, actuating the pinch valve to seal off a level of suction applied to the breast, and actuating the compression member to establish a positive pressure to pump the milk having been extracted from the breast to a location away from the breast and compression member, while maintaining the level of suction applied to the breast.

In one or more approaches, the establishment of a suction level further involves varying the suction level between a maximum suction level and a latch suction level, wherein the latch suction level applies less suction than an amount of suction applied at the maximum suction level, and wherein the latch suction level is applied to the breast when the compression member establishes a positive pressure. There can also be provided an approach involving monitoring pressure applied to the breast and providing pressure readings to a controller, and modifying operation of at least one of the compression member and the pinch valve to compensate for pressure changes resulting from entry of milk into the conduit. Furthermore, one or more approaches can involve returning to a milk extraction phase by coordinating movements of the pinch valve and the compression member to open up the first region and open the second region to generate suction.

These and other features of the disclosure will become apparent to those persons skilled in the art upon reading the details of the systems and methods as more fully described below.

DETAILED DESCRIPTION OF THE DISCLOSURE

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a valve" includes a plurality of such valves and reference to "the pump" includes reference to one or more pumps and equivalents thereof known to those skilled in the art, and so forth.

The publications discussed herein are provided solely for their disclosure prior to the filing date of the present application. The dates of publication provided may be different from the actual publication dates which may need to be independently confirmed.

Figure 1:
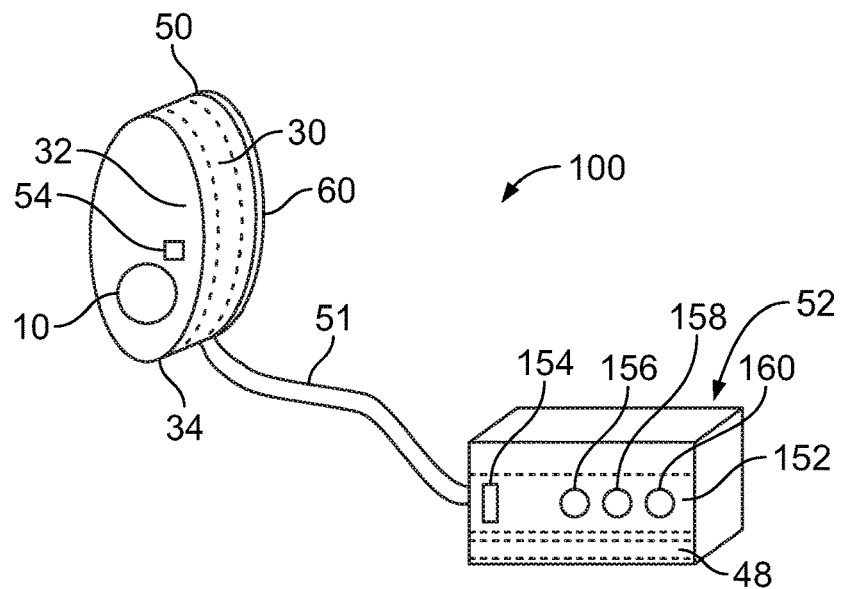
FIG. 1 is an illustration of a breast pump system according to an embodiment of the present disclosure.

FIG. 1 is a schematic illustration of components of a breast pump system 100 according to an embodiment of the present disclosure. System 100 includes one or more of a skin contact member (e.g., breast flange) 10, a pumping region 30 within a main body 34, a pressure sensor 54, tubing 32, a one-way valve 50 and a milk storage container 60.

A controller 52 can additionally or alternatively electrically connected to pressure sensor 54 drivers 44, 46 of the pumping region 30 via cable 51 and may be configured to modify the operation of the compression elements 36, 38 (e.g., pinch valve 36 and pump paddle 38) based on user input and/or input received from pressure sensor 54 (or multiple pressure sensors) that may be placed least one location to assess the pumping function and maintain an acceptable pumping negative pressure profile for a wide variety of milk expression volumes. As shown, pressure sensor 54 is placed just proximal of the skin contact member adjacent tubing 32 to measure the pressure/vacuum level within tubing 32. Alternatively or additionally, one or more pressure sensors could be placed in tube 32 upstream of compression driver 36, in between the locations of compression drivers 36 and 38 and/or downstream of compression driver 38. Further alternatively or additionally, a pressure sensor could be placed in tube 32 near, but upstream of one-way valve 50. The pressure sensor 54 (and/or flow sensor or any other sensor employed)—may be inserted into the tube 32, but is preferably designed in such a fashion such that it produces a signal that correlates to a pressure (or flow) but may not necessarily itself be in contact with the fluid and/or gas generating the pressure or flow. This arrangement that does not directly contact the milk (interior of the tube 32) is preferred to simplify cleaning of the tube 32 and skin contact member 10 or to make it cost feasible to provide the skin contact member 10 and/or tubing 32 as a disposable unit.

Figure 2:
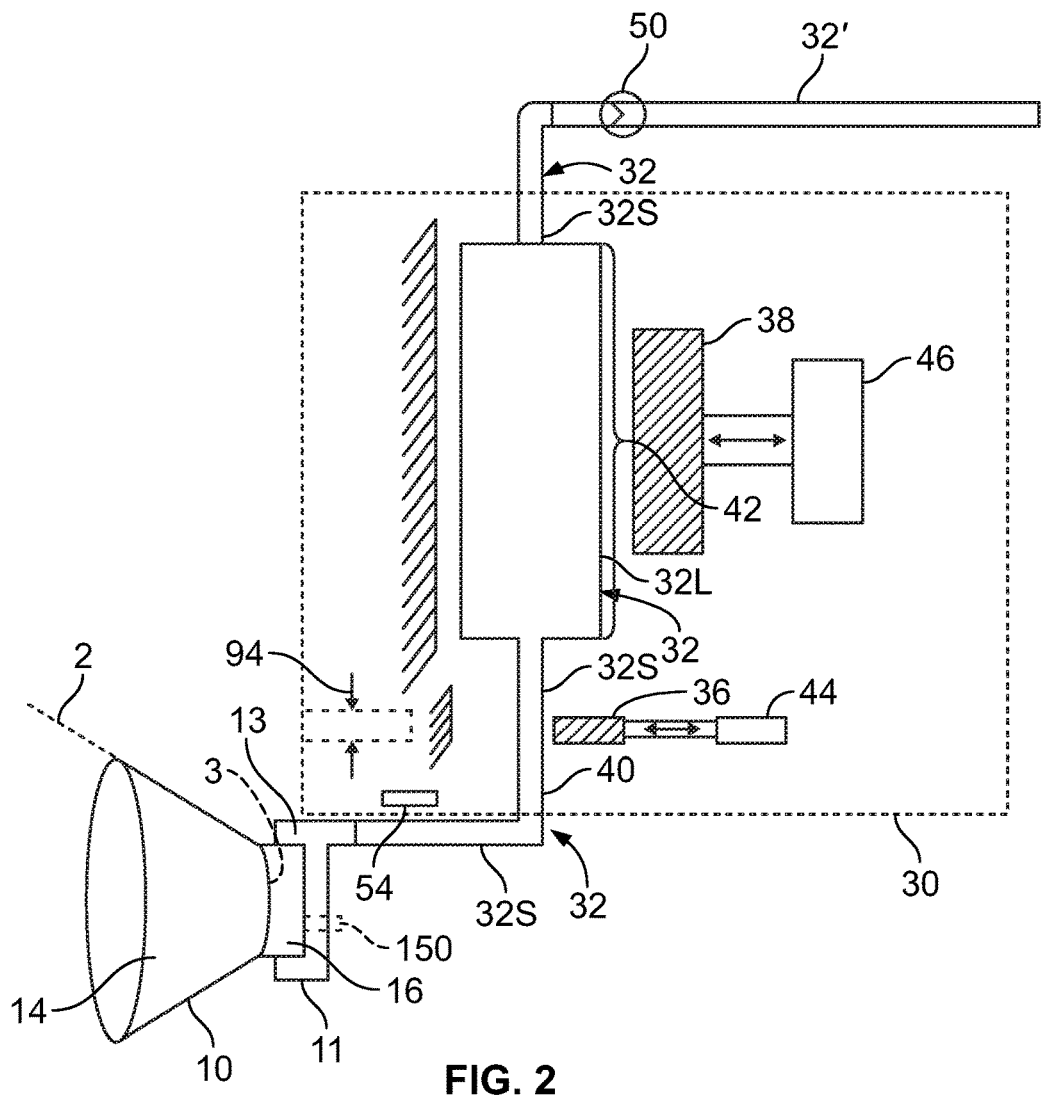
FIG. 2 is a partial view of the system of FIG. 1, according to an embodiment of the present disclosure.

Controller 52 contains control circuitry 152 configured to control the pumping operations of the system 100. Controller 52 may contain one or more batteries 48 (one battery as shown in FIG. 2) to power the system 100 by supplying electrical power for operation of the controller/control circuitry 52/152, pumping region 30 and pressure sensor 54. Alternatively, the system could be powered by AC electricity by providing the controller 52 with an AC power cord and AC power supply and plugging the system 100 into an AC power source, or by compressed gas, spring loaded power (which may offer ways to "hand crank" to power w/o electricity), gas or suction from a remote source such as a traditional breast pump uses, etc.

A power switch 154 is provided to turn the power to the system 100 on and off. A mode selector 156 is provided to allow the user to manually change pumping modes. Pumping modes are described in further detail below. A speed selector 158 is provided to allow the user to manually adjust the pumping speed, i.e., to speed up or slow down the current rate that the pumping region cycles to complete a pumping cycle. A pumping force selector 160 is provided so that the user can manually adjust the force with which the pumping stroke of each pumping cycle is applied. By increasing the force, the compression driver 38 increases the amount of vacuum increase from low vacuum to high vacuum experienced during a pumping cycle and, conversely, by decreasing the force selected, the compression driver decreases the amount of vacuum increase from low vacuum to high vacuum experienced during a pumping cycle.

FIG. 2 is a partial view of the system. Skin contact member (shown in this embodiment as a breast flange) 10 is removably attached to the system 100 by attachment to flange adapter 11 which may be integrally formed with tubing 32 or may be separately formed and attached to tubing 32 to form an airtight, liquid-tight seal. Flange 10 may be removably attached to flange adapter 11 by pressure fitting, threads, bayonet fitting, adhesive, or other equivalent means of attachment that provides an airtight, liquid-tight seal between the flange 10 and the flange adapter 11, and allows flange 10 to be readily detached from the flange adapter 11. This allows for flange 10 to be made disposable, while reducing costs compared to an arrangement in which the flange 10 and tubing are integral and would need to be disposed as a unit. This further allows attachment of flanges 10 of various sizes to meet individual user needs and preferences. Flange 10, flange adapter 11 and tubing 32 may all be made of the same materials or different materials, such as silicone or other compliant, biocompatible material, such as, but not limited to polyurethane and/or polyether block amides (PEBAX) to provide a soft interface with the breast and also provide a seal around the areola and nipple of the breast, and to provide the tubing with compliancy and resiliency for establishing a desired amount of vacuum. Breast flange 10 is configured and dimensioned to surround the nipple of the breast. The inner housing 14 of the breast flange 10 can be rigid, semi-rigid or compliant. Preferably the breast flange 10 and inner housing 14 are compliant and made from silicone or polyethylene terephthalate (PET), although other materials and combinations of materials could be used, including, but not limited to polyurethanes, polyethylene, high density polyethylene (HDPE), low density polyethylene (LDPE), polyamides, polyethylene terephthalate (PET) and/or PEBAX. For the embodiments where there is compliance, inner housing 14 is capable of iteratively opening and closing during extraction of milk from the breast using system 100, thereby simulating a feeding cycle similar to the sequence of the tongue against the nipple when a baby is suckling.

An open segment 16 within the housing of breast flange 10 is configured and dimensioned to allow for at least some clearance and space in front of the nipple to permit milk to exit the nipple even when the nipple is pulled forward by suction. Open segment 16 is typically distinct from the main body of the flange 10 as the flange 10 tapers to meet the generally non-tapered chamber of the open segment 16. In the embodiment shown in FIG. 2, an outlet 13 is formed at or near the top of the proximal end portion of the segment 16 when the flange 10 is attached to the breast 2. This ensures that any air present between the breast 2 and the flange 10 is expelled initially, prior to pumping of milk. In an alternative embodiment, outlet 13 is formed at or near the bottom of the proximal end portion of the segment 16 when flange 10 is attached to the breast 2. This placement of the outlet 13 facilitates pumping milk out of the flange 10 after a breast pumping session has ended and the flange 10 has been removed from the breast 2. Further alternatively, the outlet 13 can be formed intermediate the top and bottom of the proximal end portion of the segment 16 when flange 10 is attached to the breast 2. This placement facilitates some extraction of air out of the space in the flange 10, while also facilitating pumping milk out of the flange 10 when the flange has been removed from the breast 2. Resilient tubing 32 is in fluid communication with and extends proximally from the proximal end of flange adapter 11, and is therefore also in fluid communication with breast flange 10 when breast flange 10 is attached to flange adapter 11. Resilient tubing 32 may have the same inside and outside diameter dimensions over the length thereof and the same hardness, compliance and resilience ratings. Alternatively, different portions of the tubing may have different dimensions and/or resiliency and/or hardness characteristics. For example, the embodiment of FIG. 2 shows the portion 32L of tubing 32 that interacts with compression element 38 has a substantially larger inside and outside diameter than the inside diameters and outside diameters of the portions 32S of tubing 32 upstream and downstream of portion 32L. The larger portion has been labeled 32L and the upstream and downstream, relatively smaller diameter portions have been labeled 32S. The relatively large volume of tubing region 32L allows compression element 38 to apply a longer stroke for generating vacuum than would not otherwise be available if this portion has the same dimensions as 32S. This allows for not only higher vacuum levels to be generated, but also for finer control of vacuum level variations provided over the course of a pumping stroke, and reserved vacuum capability, if needed. The relatively smaller diameters of the tubing portions 32S help to minimize the capacity of milk that is stored in those sections prior to being pumped out to the collection container 60. These smaller diameters also make the tubing 32S (when made of the same material and thickness as tubing 32L) to be somewhat less compliant than 32L, again reducing the amount of milk contained in the tube prior to it being pumped into the collection container 60.

The conduit regions 32L and 32S do not need to be tubular or circular in cross section. When tubular, the cross-sections may be oval square, other polyhedral shape, non-symmetrical, or non-geometric shape. In one embodiment where tubing/conduit regions 32L and 32S are circular in cross section, region 32L has an inside diameter of 0.375 inches and a wall thickness of 0.094 inches, and region 32S has an inside diameter of 0.104 inches and a wall thickness of 0.044 inches. Tubing 32 (including portions 32S and 32L) can have inside diameter dimensions in the range of 0.040 inches to 1.0 inch and wall thickness dimensions in the range of 0.006 inches to 0.156 inches. The hardness of the materials used to make tubing regions can be in the range of 30 to 85 Shore A Durometer, typically in the range of 50 to 65 Shore A Durometer. However, these values may vary, depending upon the geometry of the portions 32S and 32L. Also, the material(s) used for the portions 32S, 32L is chosen for the ability to rebound against the high vacuum generated by the system. If the rebound is generated in another way, or assisted with another feature, the wall thicknesses and durometers of portions 32S and 32L can be relatively lower. Examples of assist features include, but are not limited to: ribbed reinforcement of portion 32L; attachment of compression members 36, 38 to portions 32S, 32L, respectively; and/or provision of one or more biasing members such as a spring to provide or assist in providing rebound force.

Two active compression elements 36, 38 are operable to compress and allow decompression of the resilient tube 32 at compressible regions 40 and 42, respectively. Although the preferred embodiment uses two active compression elements as shown, alternative embodiments could have three or more active compression elements. Resilient tube 32 is preferably made of silicone, but could alternatively be made from other thermoplastic elastomers exhibiting the desired performance characteristics described herein, including, but not limited to polyurethanes and/or PEBAX.

Different regions of tube 32 may be of different materials/ material properties. The regions can all be molded of same material, overmolded, glued or otherwise attached, constructed, etc. In at least one embodiment, the compressible regions may have different properties from other non "active" regions—such as those non active regions being rigid (e.g., tubing 32S upstream and/or downstream of the pumping region and/or other non-active regions) to improve pumping efficiency by reducing energy losses due to expansion and contraction of regions not intended to be active. The non-active regions can be made of different materials from the active regions or otherwise reinforced. The various regions can also be other shapes than circular in cross-section. The material(s) from which the compression regions 40, 42 of tube 32L are made can be the same as that of the breast flange 10 and flange adapter 11, only differing optionally by thickness. Further alternatively, the material(s) from which the compression regions 40, 42 are made can differ from one another. A factor in the choice of material and material thickness and length is the response time required to expand the compression regions 40, 42 from a target compressed shape/state to an original, unbiased rebound configuration (e.g., return to a full cylindrical shape in the embodiments where tube 32L is cylindrical), force required to compress to the desired target compressed shape, radial force (pressure drop) achieved when allowing the tube 32L to self-expand, volume within the inside diameter of the tube 32 regions 40 and 42, compatibility with the materials for the remainder of the breast flange 10 (nipple housing), resiliency to maintain its material properties through multiple wash, aging and use cycles, surface and depth characteristics such as material transparency, clarity and texture/ feel against the skin, visual appearance, mechanical durability, tear resistance, shape memory, soft/hardness, biocompatibility, non-reactivity and free of leachables, heat/ cold resistance, etc.

Examples of tubes 32 include, but are not limited to: silicone tubing, such as used in peristaltic pumps, both platinum-cured and peroxide-cured silicone tubes. Dimensions can range greatly in inside diameter and wall thickness, as noted above. Walls may also range to impact properties, with preferred embodiments in the ranges noted above. Inside diameters and wall thicknesses can be varied, as needed, with ensuring appropriate lengths of tubing 32. Further alternatively, pumping regions 40, 42 do not need to be in the shape of a cylindrical tube, or even a tube at all, but can be any volume shape that can be changed/compressed. For example, the cross-section could be oval, square, trapezoid, etc. as needed to fit the device space. Other factors that are considered for material choice and geometry of portions 32L and 32S include characteristics of the material for hysteresis, under the pressures (vacuum levels) experienced during use over repeated cycles, elongation, tensile strength modulus of elasticity and tear strength, etc.

In the embodiment of FIG. 2, compression element 36 is minimized, so that length 94 is in the range of about 1 to 4 mm, preferably about 1 to 2 mm, so that it is effective to seal off the tubing 32S, but operates in concert with compression element 38 to establish sufficient suction/vacuum for extracting milk. The width of compression element 36 is typically at least as great as the inside diameter of the tubing 32S, most typically greater than or equal to the outside diameter/width of portion 32S, but could be equal or slightly less than the inside diameter or less than the outside diameter but greater than the inside diameter, since the compressive action of the compression element 36 against portion 32S extends slightly past the ends of the compression element 36. By minimizing the length 94, less force is required to seal off the tube 32S, as compared to the force necessary to seal the tube 32S using a compression element 36 having a greater length. Also, the relatively smaller diameter of tube 32S compared to tube 32L allows the tube 32S to be sealed with a relatively shorter throw of the compression element 36, thereby reducing power requirements of the system 100, which can lead to a smaller driver 44 being used, a smaller battery 48 due to the lower energy requirements, and/or longer operational time before the system 100 needs to be recharged or plugged in to an AC power source (in embodiments where this is possible). Response times of the system 100 may also be faster. The time required for the compression element 36 and the tube 32S to completely seal at 40 or release may be shorter. Also, there is less volume that is moved on the final close during feedback, so if the sealing element 36 is near closing and waiting for the pressure feedback controlling the larger compression element 38 to establish the desired pressure before closing, the smaller profile corresponds with less volume change on that final seal motion. Therefore the sealing can be more precisely and accurately controlled.

Figure 3:
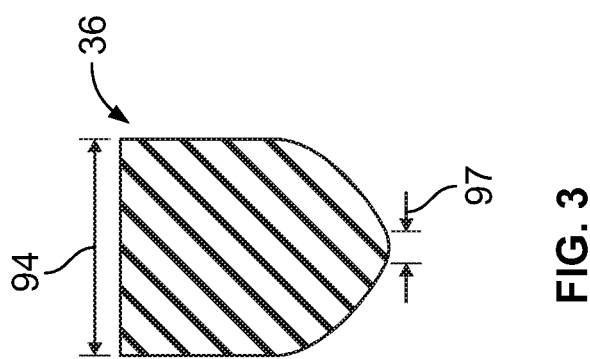
FIG. 3 shows a longitudinal-sectional view of a compression element of the system according to an embodiment of the present disclosure.

FIG. 3 shows a longitudinal-sectional view of compression element 36. The length 94 at the proximal end of the compression element 36 is in the range of about 0.25 inches to 1.0 inch, in at least one embodiment, about 0.75 inches, and tapers to a length 97 of about 1/16 inch to about 3/16", typically about 1/8 inch. The compression element tapers nearly to a point, but not too sharp to run the risk of cutting the tube 32S. Thus, the initial contact surface of compression element 36 against tube 32S is minimized to minimize the amount of force required to initiate collapsing of the tube 32S. Because the contact surface spans across the entire width of the tube 32S, it pinches off the tube 32S against the anvil surface 2320, thus sealing this location in an airtight, liquid-tight manner, so that the suction level experienced by the breast does not change as the compression element 38 works to change the suction level in the tubing 32 downstream of the pinch valve 36.

As shown in FIG. 2, the compression elements 36 and 38 are driven by dedicated compression drivers 44, 46. Alternatively, compression elements 36 and 38 could be driven by a single compression driver, controlled by controller 152 to drive each of the compression elements 36, 38 in the manner desired. As shown, the compression elements 36, 38 comprise pistons, but alternative features could be used to accomplish the same function, such as lever arms, screw drives, clamps, cams, pincers, rollers, magnets, electro-magnets, linear drives, solenoids, gears, stepper motors, or other features, respectively. The compression surfaces of the compression elements 36, 38 may be formed as flat paddles to allow complete crushing of the tube 32 without residual volume. Alternatively, one or both compression surfaces may be formed with a "V-shaped" or "U-shaped" edge (such as in the embodiment shown in FIG. 3) aligned axially with the tubing 32 to allow less force to compress tubing 32 to the same distance of compression, relative to a flat surface paddle. Further alternatively, or additionally, one or both compression surfaces may be formed with a cross edge (perpendicular) to axis of tubing. This provides a relatively small surface area allowing less force to completely seal tubing 32 at the location of the cross edge. However this also provides a relatively minor volume change/pressure change capability.

One or both compression surfaces may be formed as roller paddles having curved surfaces so that the compression action is not simply straight into the tubing 32. The roller paddle surface can roll on the tubing 32 to seal and move in a given direction. Dual action of the roller can be provided, so that, initially the roller comes down in compression against the tube 32 and seals the tube 32, which may be capable of being performed with relatively low force. Secondarily, the roller paddle can roll the compression surface in a predetermined direction along the length of the tube 32 and squeeze a volume of milk or air or combination in a given direction. This can be useful to maximize both increase and decrease in pressure changes and fluid movement.

Each compression element 36, 38 is operatively connected to a driver 44, 46, respectively, for independent but coordinated driving and retraction of the compression elements 36, 38. When electrically-powered drivers are used, a battery 48 is electrically connected to the drivers 44, 46 and supplies the power necessary to operate the drivers 44, 46 to drive the compression and retraction of the compression elements 36, 38.

A sensor 54 is used to provide feedback to the controller 52 for controlling the pumping cycles to achieve and/or maintain desired vacuum levels. Sensor 54 is preferred to be a pressure sensor but could also be a flow, temperature, proximity, motion sensor or other sensor capable of providing information usable to monitor the safety or function of the pump mechanism of system 100. Preferably sensor 54 is located at or nearby where the tip of the nipple 3 of the breast 2 is located to determine actual pressure being exposed to the breast 2/nipple 3, but other sensors 54 may be located within the system 100, for example, near, proximal or distal where the one-way valve 50 is located, and can be used to monitor other features such as container 60 contents or expulsion pressure or flow rate. With at least one sensor 54 present, by monitoring either flow or pressure directly or indirectly and also taking into account the cycles and actual positions of the compression elements 36, 38 over time, such as positioning one or more sensors proximal or distal thereto, it is possible to derive/calculate approximately the volume of milk produced during a pumping session as well as understand the flow-rate at any particular time in a pumping session. The accuracy of this measurement is greatest when there is no leak of air around the breast 2 and also when there is negligible air within the tube 32, after elimination by a few cycles of the pumping mechanism.

A one-way valve 50 such as a duckbill valve or other type of one-way valve is provided at the end of tube 32 where it enters the milk collection/storage container 60 or is connected in fluid communication with another tube 32' that can connect to a milk collection/storage container 60. Valve 50 prevents back flow of milk into the tube 32, as well as preventing air from entering the proximal end of the tube and thereby maintains the suction (vacuum) level in the tube 32. Valve 50 can further be designed to open in the reverse direction, for safety purposes, if a predetermined maximum vacuum level is exceed in tubing 32, such as greater than 250 mm Hg vacuum (−250 mm Hg pressure), for example. In at least one embodiment, the pressure at which the valve 50 opens to allow flow into the milk collection container 60 is about 25 mm Hg. In an alternative embodiment, a pressure relief valve 150 can be provided in the system 100, such as in the flange 10, adapter 11 (as optionally shown in FIG. 2), or other location along tubing 32. The pressure relief valve 150 can be configured to release at vacuums greater than a predetermined amount, (e.g., vacuums greater than 250 mm Hg (pressures less than −250 mm Hg), or some other predetermined maximum vacuum level). The one-way valve 50 can be configured and designed such that it allows fluid to flow through it only when the pressure in tubing 32 is positive, e.g., about 25 mm Hg, or some other predesigned "crack pressure". The action of the compression elements cycles between increasing vacuum when the compression elements move in a direction away from tube 32 and decreasing when the compression elements compress the tube 32, but typically should not increase the vacuum to greater than the predetermined maximum vacuum. As the compression elements 36, 38 compress the tube 32, the pressure in the system 100 goes up and reaches the minimum suction level (e.g., −60 mmHg, −30 mm Hg, or some other predetermined minimum suction level), at which time the compression member (pinch valve) 36 seals off portion 32S thereby maintaining the minimum suction against the breast 2. Continued compression of portion 32L by compression member 38 continues to increase the pressure downstream of compression member 36, until the crack pressure is reached (e.g., 25 mm Hg or some other predetermined, positive crack pressure), that opens the one-way valve 50. The compression elements 36, 38 continue compressing tube 32, pumping fluid (milk) through the one-way valve 50 and into the collection container 60 until the compression element 38 reaches an end point in travel (typically before "bottoming out" against the anvil). The end point in travel of the compression element 38 against portion 32L may be predetermined, or may be calculated on the fly by the controller 52 using feedback from pressure sensor 54 and feedback from the driver of the compression element 38, from which the controller 54 can calculate the relative position of the compression element 38 over the course of its travel. The compression member 36 remains closed throughout this process, as it is used to seal off the tube 32 the entire time that the compression element 38 is pumping milk out of the region 42 and into the collection container 60). As the compression elements 36, 38 reverse direction and pull away from the tube 32, they start the cycle again.

FIG. 3 is a perspective view of a portion of system 100 according to an embodiment of the present disclosure. This view is oriented in the manner that the system would be oriented during use upon attachment to a breast 2, with the breast flange 10 extending from the lower end portion of housing 34. As noted previously, breast flange 10 is readily detachable from the flange adapter 11 (not shown in FIG. 3). Additionally, housing lid 35 is removable from housing 34 to expose the tubing 32 and pumping mechanism 30. Housing lid 35 may be attached to housing 34 using screws 37, snap fit, or other mechanical arrangement that allows easy attachment and detachment of the lid 35 to and from the housing 34. Protective struts 43 extend from the housing 34 and through tube 32S/valve 50 to protect the tube 32S/valve 50 from damage that might otherwise be incurred from inadvertently contacting this portion of the system with another object.

Figure 4:
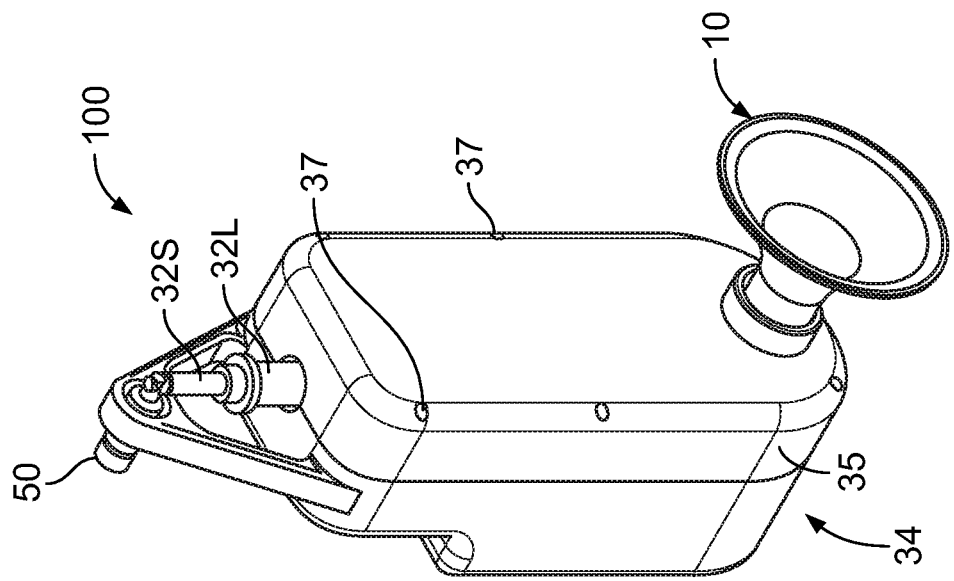
FIG. 4 is a perspective, partial view of a system according to an embodiment of the present disclosure.
Figure 5:
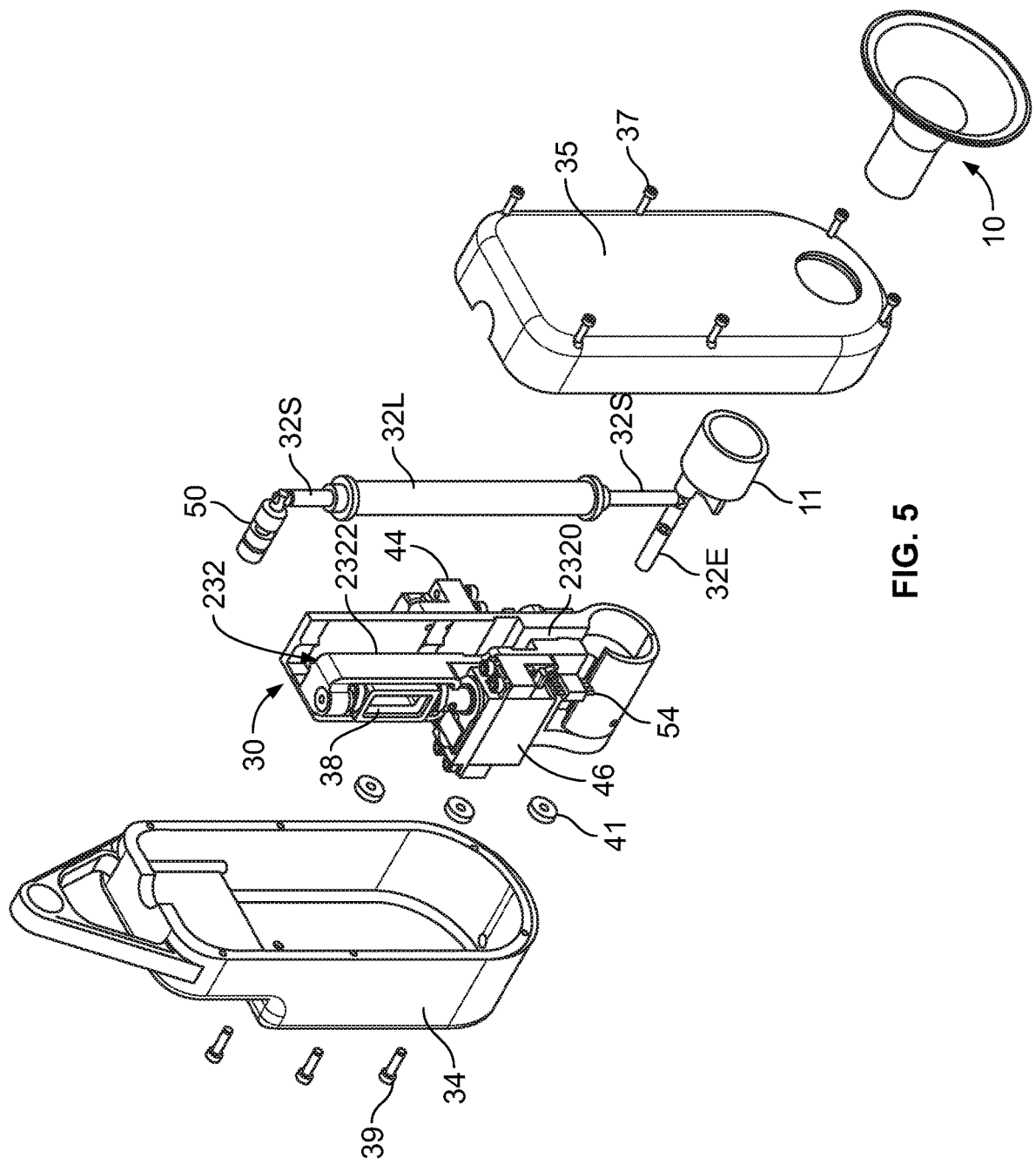
FIG. 5 shows an exploded view of the embodiment of FIG. 4.

FIG. 5 shows an exploded view of the embodiment of FIG. 4. The tubing assembly including small tube portions 32S, large tube portion 32L and extension tube 32E that is in fluid communication with pressure sensor 54, snaps in or forms a friction fit in channels 232 in the pumping subassembly 30. The pumping subassembly 30 is secured in the housing 34 and covered by lid 35 using screws 37, nuts 39 and washers 41. Anvil surfaces 2320 and 2322 are formed by walls of the channel 232 against which tube portions 32S and 32L are compressed by elements 44 and 46, respectively.

Figure 6:
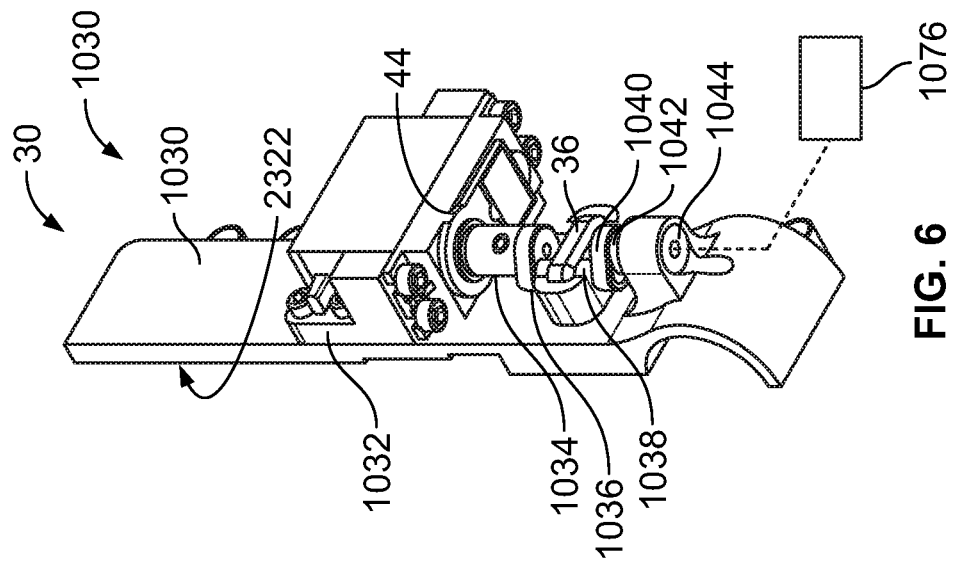
FIG. 6 is an isolated view of one side (right hand side of the subassembly shown in FIG. 5) of the pumping subassembly, according to an embodiment of the present disclosure.

FIG. 6 is an isolated view of one side (right hand side of the subassembly 30 shown in FIG. 5) of the pumping subassembly 30, according to an embodiment of the present disclosure. Driver 44 in this embodiment is a servo motor (Servo City HS-645 MG, RobotZone, LLC, Winfield, Kanas) mounted to the subassembly frame 1030 via motor mount 1032. The first compression member 36 that functions as the pinch valve is driven by motor 44 via a drive train connecting the servo motor 44 to compression member 36. In this embodiment, the drive train includes servo motor shaft 1034, servo hub 1036, rod 1038, second servo hub 1040 and shaft 1042 that is received in journal bearing 1044 mounted to the frame 1030. Together 1034, 1036, 1038, 1040 and 1042 form a crank shaft that is rotated by servo motor 44 to drive the compression member 36 toward and away from the small tubing portion 32S. The opposite surface (back side surface, not visible in FIG. 6) forms the anvil 2232 against which the large tubing section 32L is compressed.

Figure 7:
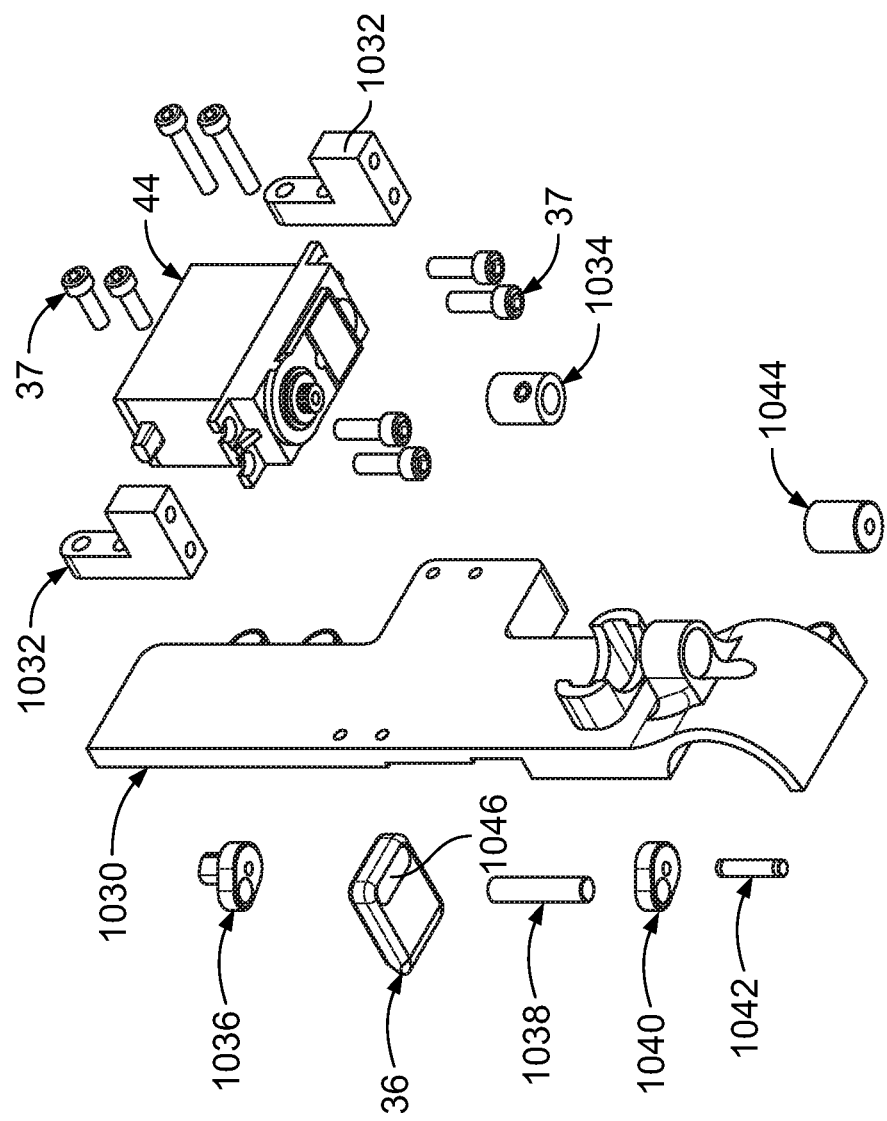
FIG. 7 is an exploded view of the components shown in FIG. 6.

FIG. 7 is an exploded view of the components shown in FIG. 6. A slot 1046 is provided in the compression member 36 through which the rod 1038 is received, and which allows the rod 1038 to oscillate back and forth as the compression member 36 is driven in and out. Screws 37 or other fasteners are used to fix the motor mounts 1032 to the frame 1030 and to fix the servo motor 44 to the motor mounts 1032.

Figure 8:
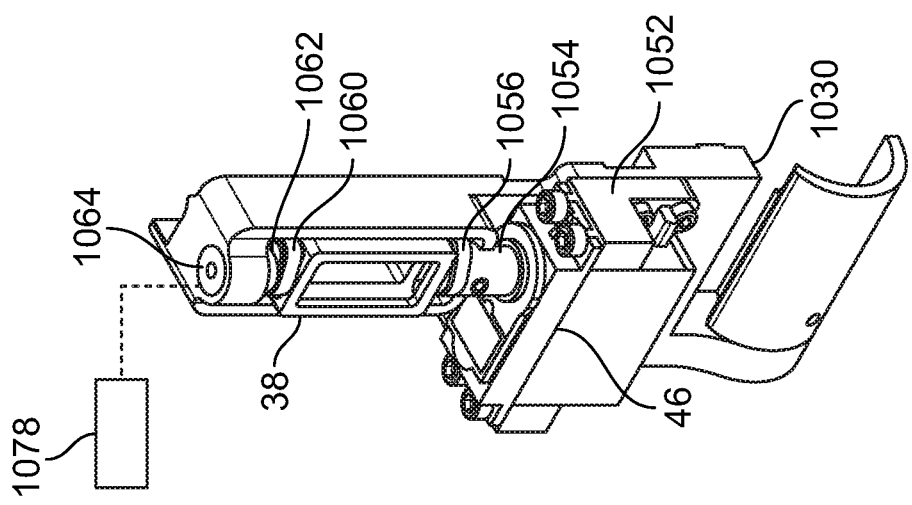
FIG. 8 is an isolated view of the other side (left hand side of the subassembly shown in FIG. 5) of the pumping subassembly, according to an embodiment of the present disclosure.

FIG. 8 is an isolated view of the other side (left hand side of the subassembly 30 shown in FIG. 5) of the pumping subassembly 30, according to an embodiment of the present disclosure. Driver 46 in this embodiment is a servo motor (Servo City HS-645 MG, RobotZone, LLC, Winfield, Kanas) mounted to the subassembly frame 1030 via motor mount 1052. The second compression member 38 is driven by motor 46 via a drive train connecting the servo motor 46 to compression member 38. In this embodiment, the drive train includes servo motor shaft 1054, servo hub 1056, rod 1058 (see FIG. 9), second servo hub 1060 and shaft 1062 that is received in journal bearing 1064 mounted to the frame 1030. Together 1054, 1056, 1058, 1060 and 1062 form a crank shaft that is rotated by servo motor 46 to drive the compression member 38 toward and away from the large tubing portion 32L. The opposite surface (back side surface, not visible in FIG. 8) forms the anvil 2230 against which the small tubing section 32S is compressed.

Figure 9:
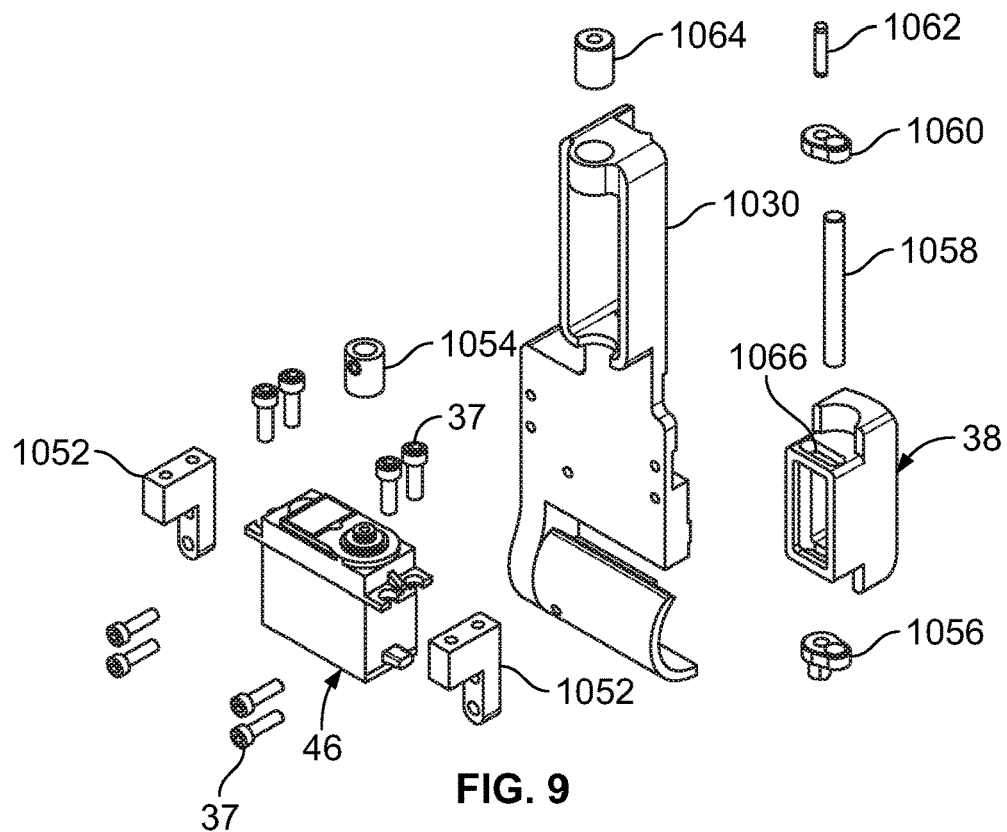
FIG. 9 is an exploded view of the components shown in FIG. 8.

FIG. 9 is an exploded view of the components shown in FIG. 8. A slot 1066 is provided in the compression member 38 through which the rod 1058 is received, and which allows the rod 1058 to oscillate back and forth as the compression member 38 is driven in and out. Screws 37 or other fasteners are used to fix the motor mounts 1052 to the frame 1030 and to fix the servo motor 46 to the motor mounts 1052.

In at least one embodiment, the servo motors 44, 46 oscillate so as to rotate the servo hubs 1036 and 1056 and associated drive trains, respectively, between a first rotational direction to advance the compression members 36, 38 against the tubing 32 and a second rotational direction to retract the compression members 36, 38 away from the tubing 32. The angles between the positions of the servo hubs 1036, 1056 at the furthest rotation in the first direction and the furthest rotation in the second direction corresponds to the stroke lengths of the compression members 36, 38 respectively, from positions in which the tubing 32 is completely closed off to positions in which the tubing is fully open, respectively. In one example, the angle for motor 44 is about 90 degrees and the angle for motor 46 is about 90 degrees. This leaves an additional forty-five degrees on either side of the rotation in reserve, that can be used, if needed, by the controller to achieve the correct pressures on each cycle. These angles can, of course, vary, depending upon design factors such as tubing diameters and resulting stroke lengths of the compression members 36, 38. A potentiometer 1076, 1078 can be electrically connected to motors 44, 46 or a portion of drive trains thereof (e.g., see FIGS. 6 and 8), respectively, and to the controller 52 to provide feedback as to the positions of the motors 44, 46 and or servo hubs, which in turn can be used to calculate the positions of the compression members 36, 38. Reduction gears are provided to reduce the speed of the respective gear train relative to the speed of the motor 44, 46. In one embodiment the reduction is about 1:200, but this will vary depending upon the performance and size of the motors used. In another embodiment the reduction is about 1:600 for motors that perform at about 6000 rpm. In general, the reduce speed of the drive train will be in a range of about 30 to 120 rpm, or in a range of about 40 to 100 rpm, typically about 60 rpm. Alternatively, the servo motors 44,46 could rotate in a single direction to accomplish movements of the compression members 36, 38 toward and away from the tubing, but this requires further movements of parts and thus more energy to accomplish the same functions, compared to embodiments in which the servo motors 44,46 oscillate.

Figure 10:
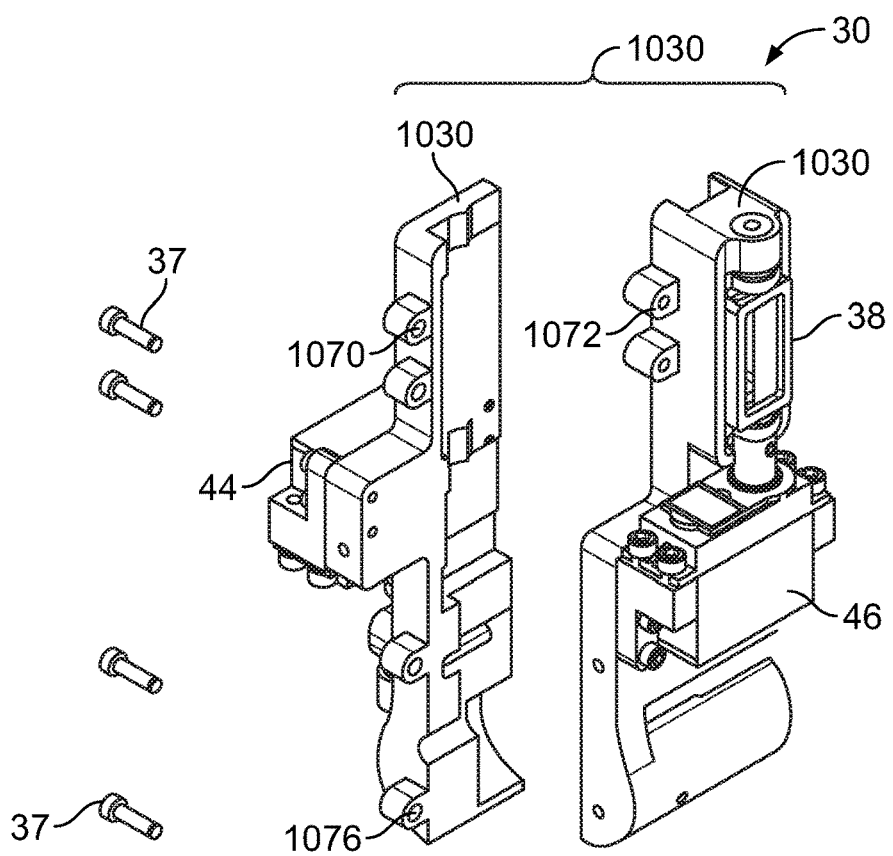
FIG. 10 illustrates how the two sides of the subassembly can be assembled and fixed together, according to an embodiment of the present disclosure.

FIG. 10 illustrates how the two sides of the subassembly 30 can be assembled and fixed together using screws or studs 37 place through screw hole mounts 1070 and into receiving mounts 1072. Receiving mounts 1072 may be threaded to mate with threads on studs 37 or screws or bolts 37 may pass through receiving mounts 1072 and fixed by nuts tightened to the back sides of the receiving mounts 1072.

Figure 11:
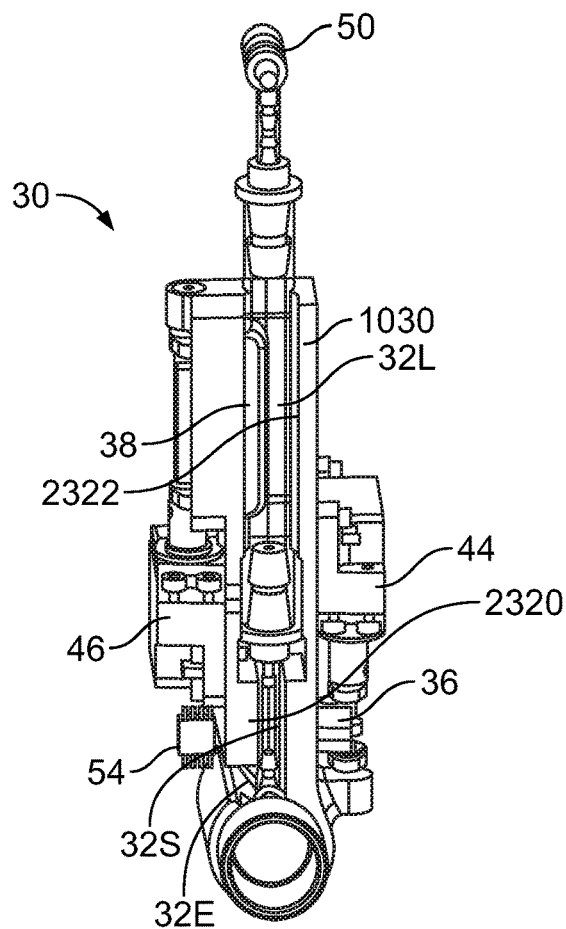
FIG. 11 illustrates an assembled subassembly according to an embodiment of the present disclosure.

FIG. 11 illustrates the assembled subassembly 30 in which the compression element 38 is driven by motor 46 (to the right in FIG. 11) against tubing portion 32L to compress tubing portion 32L against anvil 2322, and compression element 36 is driven by motor 44 (to the left in FIG. 11) against tubing portion 32S to compress tubing portion 32S against anvil 2320. The positions, speeds and relative positions of compression members 36, 38 are all controlled by controlling motors 44, 46 through controller 52.

Figure 12:
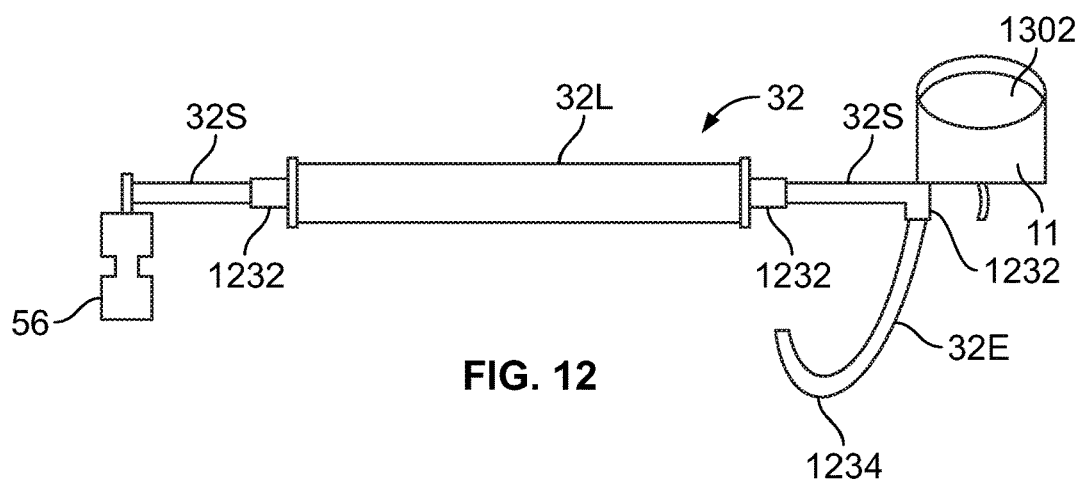
FIG. 12 shows an isolated view of a tubing assembly according to an embodiment of the present disclosure.

FIG. 12 shows an isolated view of the tubing assembly 32. The design characteristics of tubing portion 32L and the tubing portion 32S between portion 32L and flange adapter 11 are more critical than the tubing portions 32E and the portion 32S extending between 32L and one way valve 50, because the former portions are the portions that are to be compressed (and which need to expand when compression is released) by compression members 36, 38. The less critical tubing is generally selected to be relatively small in inside diameter, so as to reduce the total volume of milk contained in the overall tubing system 32. For power efficiency of the compression member 36, the tube 32S between 32L and 11 is designed to have a relatively small diameter (to reduce the stroke of the compression member 36) and to be compliant so as to be easily compressed. By keeping the stroke as short as possible and the force needed to compress the tube 32S as low as possible, this minimizes the energy expenditure required by the system 100 to operate the compression member 36. A limiting constraint regarding the compliance of the tubing 32S that is to be compressed by the compression member 36, is that it should not collapse when it is not being compressed by the compression member 36, that is, it needs to be able to withstand the internal vacuum within the tube without collapsing upon itself. In at least one embodiment, the tube 32S at region 40 can withstand vacuums up to about 300 mm Hg (−300 mm Hg pressure) when the system is designed to operate between 60 mm Hg and 200 mm Hg vacuum. It would be apparent to one of ordinary skill in the art that these design parameters could be changed in different embodiments without departing from the principles of the present disclosure. As the vacuum increases within the tube 32S, this reduces the overall force that needs to be applied by the compression member 36 to close or pinch off the tube 32S. Accordingly, tube 32 should not be designed to have a collapse strength that is much greater than the maximum operating vacuum, as the closer the collapse strength is to the maximum operating suction, the less will be the power consumption to generate the force needed to close off the tube 32S. Of course, a margin needs to be provided between the planned maximum operating suction and the collapse strength, to ensure that the tubing 32S does not collapse when it should remain open. Currently, the preferred suction margin is in the range of about 50 mm Hg to about 80 mm Hg. The lower the margin, the less ability the tubing will have to rebound in a timely matter after removal of the compression member, whereas the higher the margin, the more energy will be required to compress the tubing. In at least one embodiment, the margin can be as low as zero mmHg, and still have a sufficiently responsive device. Considering zero margin opens the potential to use the tubing 32L/32S as a safety element, preventing unwanted vacuum beyond the specified maximum suction level. The re-expansion of tube 32S occurs upon retraction of the compression member 36 under the resilient forces of the tube 32S. Assisting this re-expansion are the milk flowing into the tube 32S as it opens, as well as any air that may enter, as well as the compliance of the breast 2. Further assistance in re-expansion may be provided by one or more biasing members, such as springs, ribs, or the like. Also, the compression member 38 and/or 36 may be connected to portion 32L or 32S, respectively.

The length of the tubing portion 32S between portion 32L and adapter 11 should be as short as possible while still allowing the compression member to perform the function of sealing off (e.g., pinching off) the tube 32S. The compressible length between the adapters that connect portion 32S to 11 and 32L should be as short as possible, typically about ⅜". In at least one embodiment, this length including the portions of the tubing portion 32S that connect over the adapters is about 1.5", but this overall length can be reduced by decreasing the length of the adapters. The length of tubing portion 32L is designed so as to accommodate a volume sufficient for the compression member 38 to compress tubing portion 32L between the maximum and minimum (latch) operating suctions. In at least one embodiment, the volume contained in tubing portion 32L should be about twenty to twenty-five percent of the entire volume of the tubing 32, but could be anywhere in the range of from about five percent to about fifty percent. In one specific example, the total volume of the tubing was about 20 ml and the volume contained in tubing portion 32L was about 4 ml. In another specific example, the total volume of the tubing was 21 ml and the volume contained in 32L was 5.25 ml. The compression member 36 displaces only a small percentage of the volume displaced by the compression member 38. Preferably, the compression member 36 displaces only about one to two percent of the total volume displaced by compression member 38, but this percentage may range up to about five percent, depending upon the control parameters used and geometry of the conduit 32 and overall system 100. By replacing the connectors/adapters 1232 with more compact adapters or joining the tubing portions using a molding process, the overall volume capacity of the tubing and consequently the volume capacity of tube portion 32L can be reduced. Reduction to an overall volume of about 12-15 ml and consequently a volume capacity of 32L of about 2.4 ml to about 3 ml is possible by making the changes described.

In the embodiment shown in FIG. 12, the use of the rigid connectors 1232 requires that they extend into the tube 32L and thus require a relatively longer tube 32L to accommodate 4 ml of volume that can be resiliently driven by the compression member 38. The length of 32L in the embodiment of FIG. 12 is about 5.5 inches. By modifying the connectors in a manner as described above, the length of 32L can be reduced to about 2.7 inches, for a ⅜" inside diameter tube 32L. By changing the inside diameter of the tube 32L used, the length can be further modified, to be made shorter or longer and achieve the same volume capacity. Also, the cross-sectional shape can be altered and/or varied in size over the length of the tube 32L. Like the tubing portion 32S described above, tube 32L is designed to minimize the amount of force needed to be applied by compression member 38 to collapse the tube 32L, but has strength sufficient to withstand maximum operation suction. The collapse pressure can be the same as in the tubing portion 32S adjacent compression member 36, typically about −300 mm Hg, or in the range of about −250 mm Hg to −320 mm Hg.

Extension tube 32E is in fluid communication with pressure sensor 54, e.g., see FIG. 11. The pressure sensor is in fluid communication with tubing 32. By providing a loop in the extension tube 32E and trapping an air bubble 1234 in the loop, the pressure sensor 54 should not come into direct contact with the milk. Alternatively, pressure sensor 54 may be of a type that is not in fluid communication with the tubing 32, such as a pressure sensor 54 of a type described in co-pending provisional application Ser. No. 62/027,685, filed Jul. 22, 2014, which is hereby incorporated herein, in its entirety, by reference thereto.

Figure 13:
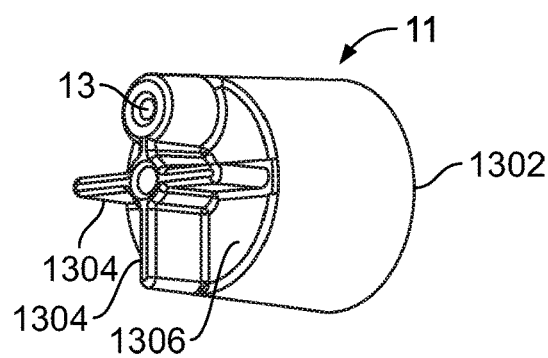
FIG. 13 is an isolated view of a flange adapter according to an embodiment of the present disclosure.

FIG. 13 is an isolated view of flange adapter 11. Flange adapter 11 includes an inlet 1302 configured and dimensioned to releasably attach to a breast flange 10 and form an airtight, liquid-tight seal therewith. Outlet 13 has already been described with regard to FIG. 2. As the outlet 13 is at or near the top of the adapter 11 when system 100 is attached to the breast 2, substantially all of the air in breast flange 10 and adapter 11 is pumped out before milk is pumped out, which greatly increases the efficiency of the pumping action when milk is eventually pumped through the tubing 32, as the tubing will contain essentially no air. Milk, being a liquid and thus non-compressible is then efficiently pumped without losses in the pumping strokes that would otherwise occur due to compression and re-expansion of air if air is in the system. Also, because the milk is pumped upwardly through the tubing, against gravity, any air present will tend to migrate up to the valve 50 where it is expelled from the system. Adapter 11 may be formed of the same materials as tubing 32 and breast flange 10, as described above, or of different materials. Ridge extensions 1304 are formed to extend from the proximal surface of proximal wall 1306 to reinforce proximal wall 1306 against excessive flexing as pressure changes are applied within the tubing 32.

The tubing assembly 32 may be provided to be washable and reusable. Alternatively, one or more components of the tubing assembly 32 may be produced as disposable components. In any case, the tubing assembly 32 can be easily replaced, as it made to be removable, even when considered to be reusable, for cleaning.

Figure 14A:
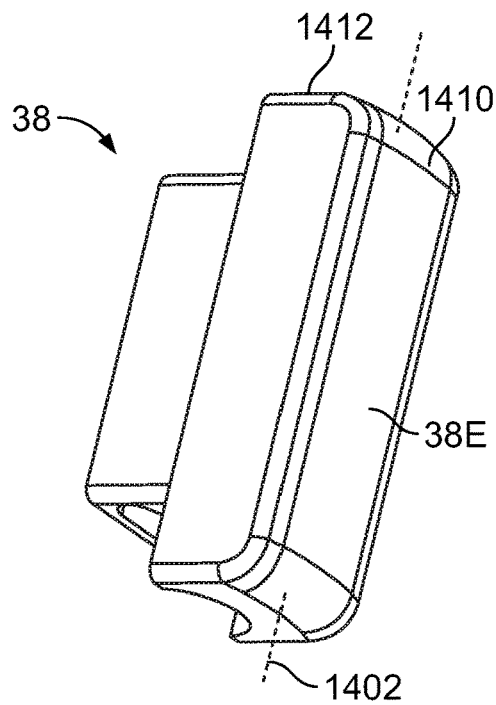
FIG. 14A is a perspective view of a second compression member according to an embodiment of the present disclosure.
Figure 14B:
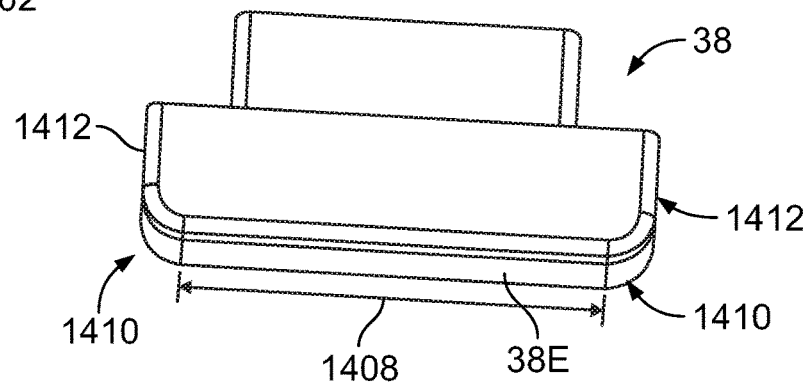
FIG. 14B is a side view of the compression member of FIG. 14A.
Figure 14C:
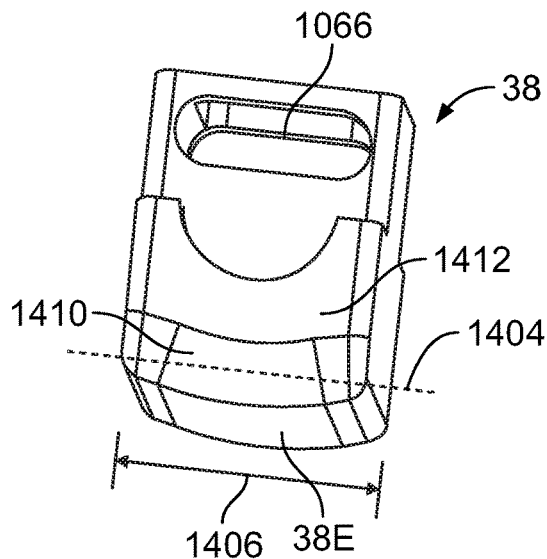
FIG. 14C is an end view of the compression member of FIG. 14A.

FIG. 14A is a perspective view of compression member 38. FIG. 14B is a side view of compression member 38, and FIG. 14C is an end view of compression member 38. The contact surface 38E that contacts the tube portion 32L to compress the tube portion 32L is convex in the transverse direction 1404 (normal to the longitudinal axis 1402) as best seen in FIG. 14C, and is not curved in the longitudinal direction, as can be observed in FIGS. 14A-14B. The width 1406 of contact surface 38E is typically at least as great as the outside diameter of the tubing portion 32L. In one example, the tube portion 32L had an outside diameter of 9/16" and contact surface 38E had a width 1406 of ¾", but could be modified to be smaller or larger as long as it can sufficiently withstand the forces applied to it by compression member 38. In the embodiment shown, the radius of curvature of the convexity in the transverse direction is the same as the inside radius of the tube, e.g., 3/16", but could be a radius of curvature within a range of about 0.0625" to about 0.375". The length 1408 of contact surface 38E will vary depending upon the dimensions of the tube portion 32L that is to be compressed. In the embodiment shown, the length 1408 is 2.7 inches, but can vary within a range of from about 0.135 inches to about 5.4 inches. The end portions 1410 between the contact surface 38E and the end surfaces 1412 of contact member 38E are radiused to prevent damage to the tube portion 32L during compression thereof. The anvil surface 2322 against which the compression member 38 compresses the tube portion 32L is typically a flat surface, but can alternatively be made concave to match the radius of curvature of surface 38E or with a greater radius of curvature than that of surface 38E. The shapes of the surfaces 38E and 2322 are optimized for the most energy efficient design for providing a predetermined volume pumping capability per stroke. The anvil surface 2322 may be further contoured to facilitate stabilization of tube portion 32L against side-to-side movements to ensure accurate registration and contact of the contact surface 38E against the tube 32L during initial contact of the surface 38E against the tube 32L and throughout the stroke.

Figure 15A:
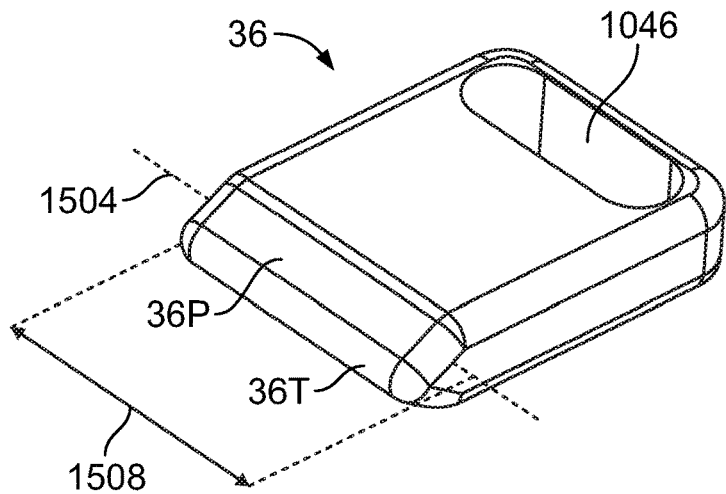
FIG. 15A is a perspective view of a first compression member according to an embodiment of the present disclosure.
Figure 15B:
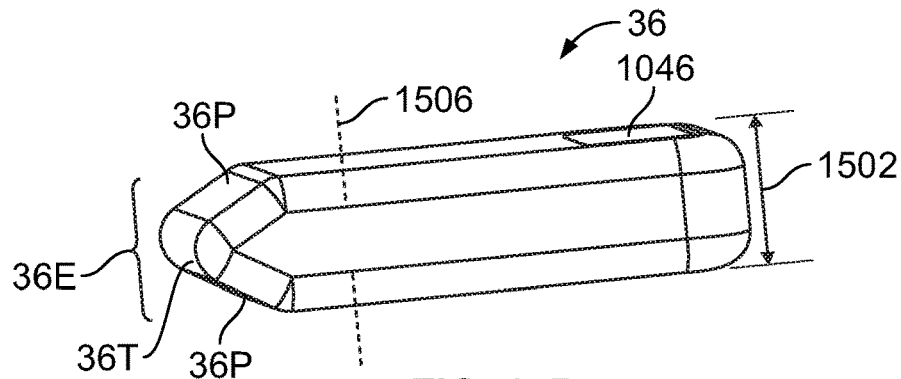
FIG. 15B is a side view of the compression member of FIG. 15A.
Figure 15C:
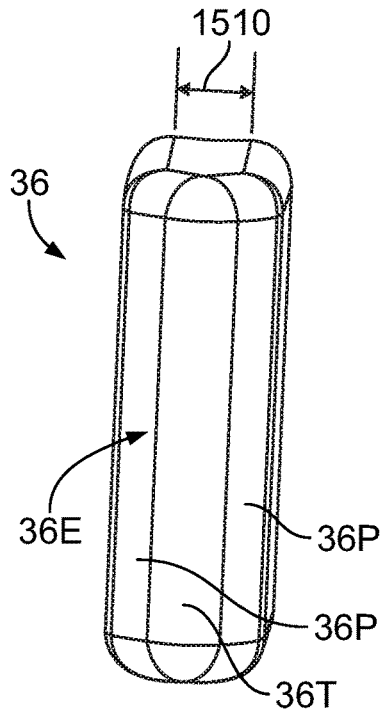
FIG. 15C is a view facing the contact surface of the compression member of FIG. 15A.

FIG. 15A is a perspective view of compression member 36. FIG. 15B is a side view of compression member 36, and FIG. 15C is a view facing the contact surface 36E of compression member 36. The contact surface 36E that contacts the tube portion 32S to compress the tube portion 32S is convex at the tip 36T and tapers along peripheral contact surfaces 36P to the full length 1502 of the compression member 36. The peripheral contact surfaces 36P may be flat (planar) as illustrated in FIGS. 15A-15C or, alternatively, could be convex. Tip 36T is convex when traveling along lines on the surface of the tip 36T that are aligned with the longitudinal axis, and is not curved in the width direction 1504, as can be observed in FIG. 15A. The width 1508 of contact surface 36E is typically at least as great as the inside diameter of the tubing portion 32S that it compresses, but may be slightly less, or greater. In one example, the tube portion 32S had an outside diameter of 0.192" and contact surface 36E had a width 1508 of 0.240". In the embodiment shown, the radius of curvature of the convexity of 36T in the transverse direction is 0.0625" (1/16"), but could be a radius of curvature within a range of about 1/32" to about ¼". The length 1502 of contact surface 36E is minimized to reduce the energy required to seal off (e.g., pinch closed) the tube portion 32S. In the embodiment shown, the length 1502 is 0.75", but can vary within a range of from about 0.25" to about 1.0". The tip 36T further minimizes the length so as to imitate the compression of the tube 32S with as little force as possible. In the embodiment shown, the length 1510 of tip 36T is ⅛", but this length can vary within a range of from about 1/16" to about 3/16". The anvil surface 2320 against which the compression member 36 compresses the tube portion 32S is typically a flat surface, but can alternatively be made concave to match the radius of curvature of surface 36T or with a greater radius of curvature than that of surface 36T, or with a radius of curvature equal to or greater than the radius of curvature of 36T that tapers to follow the contours of surfaces 36P. The shapes of the surfaces 36E, 36P and 2320 are optimized for the most energy efficient design for providing the sealing function of the compression member (e.g., pinch valve). As such, the amount of volume displaced by compression member 36 is minimized to minimize the energy requirements for compressing tube 32S. The smaller the contact surface of tip 36T is, the less will be the energy requirement to initiate buckling of the tube 32S during compression. At the same time, the tip should not be designed too sharp, such as in the form or a knife edge or other tip that converges substantially to a line, as this runs a great risk of cutting or other damage to the tube 32S during repeated compression strokes. As a result, the shape of tip 36T has been found to be an optimum compromise of these competing design constraints. The anvil surface 2320 may be further contoured to facilitate stabilization of tube portion 32S against side-to-side movements to ensure accurate registration and contact of the contact surface 36E against the tube 32S during initial contact of the surface 36E against the tube 32S and throughout the stroke.

Figure 16:
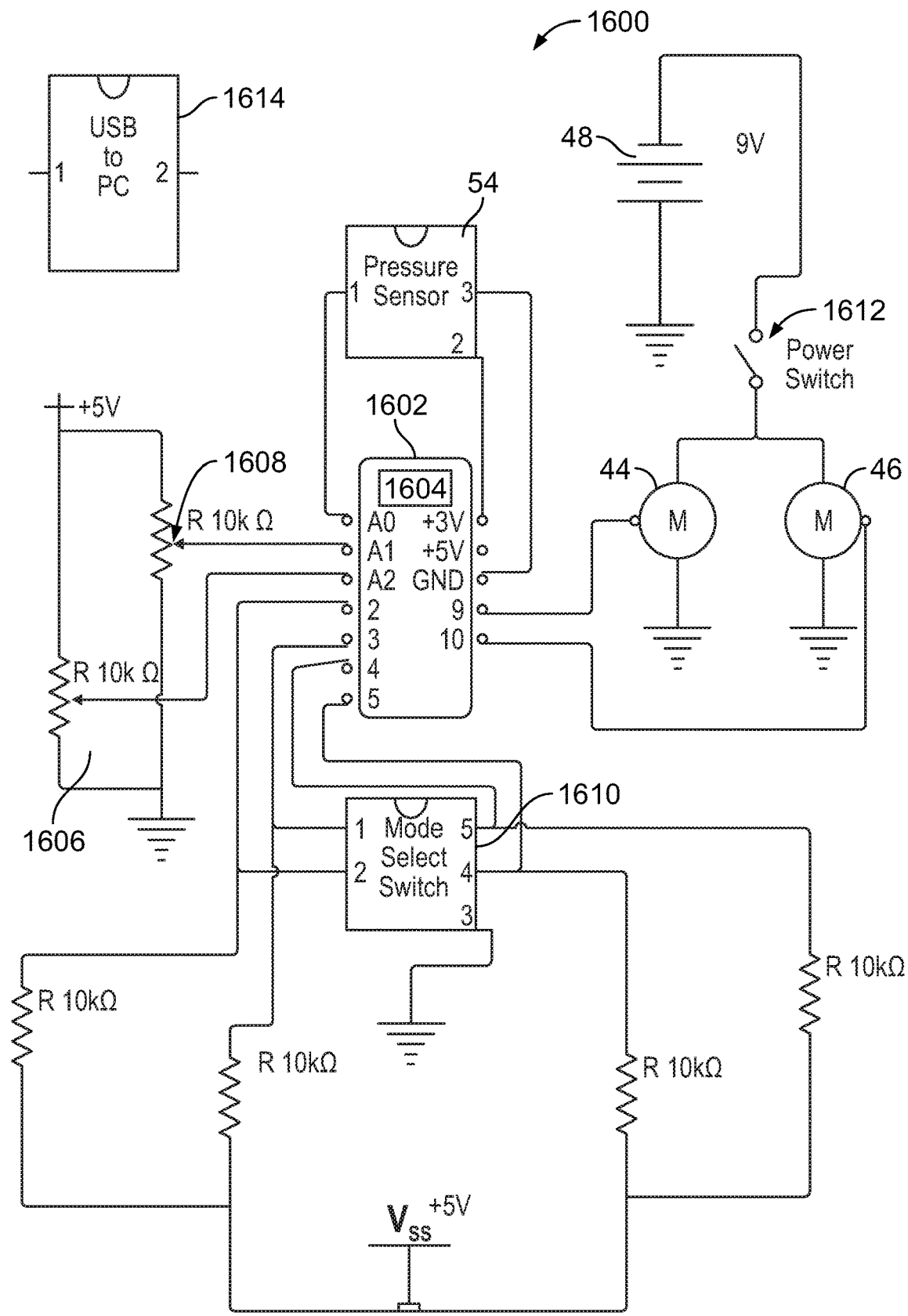
FIG. 16 shows a schematic circuit diagram of componentry used to control a system according to an embodiment of the present disclosure.

FIG. 16 shows a schematic circuit diagram of componentry used to control system 100 according to an embodiment of the present disclosure. Controller 52 includes a microcontroller board 1602 (e.g., Arduino Mega 2560, or other microcontroller board of comparable functionality). A microcontroller processor 1604 is provided on board 1602 to process the control functions for reading pressure (and/or any other function being sensed, such as flow, or other function) and controlling the functions of the motors 44, 46, as well as monitoring speed, direction and positions of the motors 44,46 and compression members 36, 38. A variable resistor/potentiometer 1606 is provided for user input to adjust the maximum vacuum achieved during a cycle of a pumping profile. The user adjusts the potentiometer 1606 using pumping force selector 160. A second variable resistor/potentiometer 1608 is provided for user input to control the speed of the pumping, i.e., to adjust the period of the pumping cycle. The user adjusts potentiometer 1608 using speed selector 158. A mode select switch is provided for selection of different modes/profiles of pumping performance by the system 100. Different profiles/modes can be selected by the user by operating the mode selector 156 to select one of the modes provided in the mode select switch 1610. The power switch 1612 is turned on and off by operation of power switch 154 by the user to connect or disconnect the battery 48 to or from the circuits.

Figure 17:
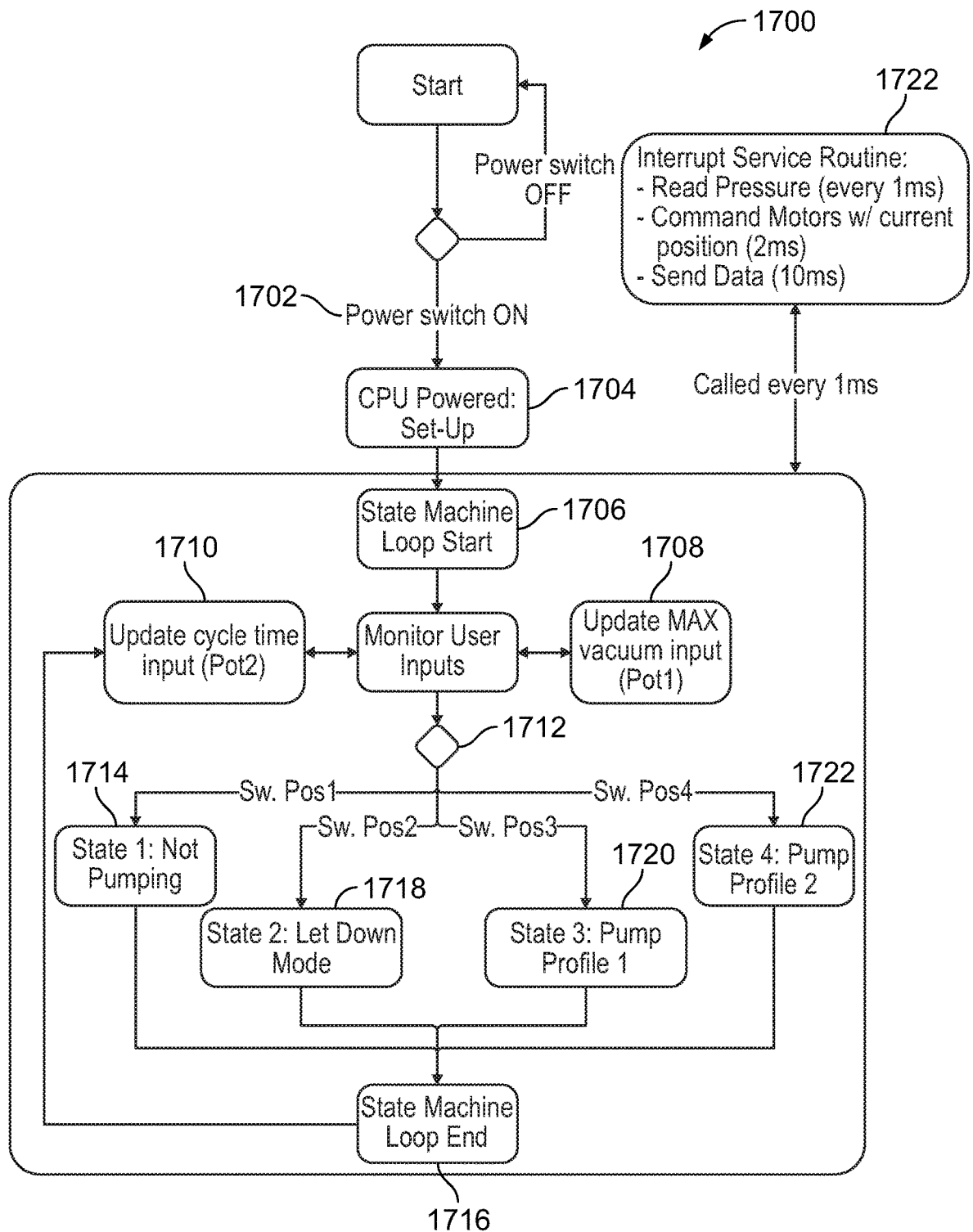
FIG. 17 is a flow chart showing events that may occur during operation and control of a system according to an embodiment of the present disclosure.

FIG. 17 is a flow chart 1700 showing events that may occur during operation and control of system 100. To operate the system, the power switch 154 is operated at event 1702 to close the switch 1612 and supply electrical power to the system 100. Upon receiving electrical power, the processor 1602 powers up and initializes at event 1704. Once initialized the processor 1602 can begin processing. The processor in this embodiment functions as a state machine and the state machine processing loop begins at event 1706. User inputs (from controls 156, 158, 160) are monitored at event 1706. If the user has operated the selector 160 to change the maximum vacuum achieved per cycle, then processor 1602 updates the maximum vacuum pressure at event 1708 to be achieved in pumping cycles going forward. If the selector 160 has not been changed, then the maximum vacuum pressure remains at the current level stored by the state machine. If the user has operated the selector 158 to change the speed (cycle period) of pumping, then processor 1602 updates the cycle period (cycle time) at event 1710. If the selector 158 has not been changed, then the cycle time remains at the current cycle time stored by the state machine.

At event 1712, the processor 1602 executes the mode of pumping operation currently selected by the mode selector 156. If the mode selector 156 is in the off position (State 1), then no pumping or operation of the motors 44,46 is performed in this iteration of the loop and processing continues from event 1714 to 1716 and performs another iteration of the loop starting again at event 1706. If the mode selector 156 is in the let down mode position (State 2), the let down profile is performed at event 1718. This mode is typically selected at the initiation of a milk extraction session. The processing and functioning of the system continues in the let down mode until such time as the user changes the mode using mode selector 156, or until the system is powered off. If the mode selector 156 is changed to select another pumping mode, the processor at event 1712 receives input regarding the change in mode selector at event 1712 and commences performing the selected mode/pumping profile (e.g., State 3 or State 4, as shown in FIG. 17 at events 1720 and 1722, respectively).

An interrupt service routine 1722 is called at predetermined time intervals (e.g., every 1 ms for the embodiment shown in FIG. 17, but could vary with different embodiments) to receive pressure reading data from pressure sensor 54. In one embodiment, the pressure reading is received in real time every 1 ms and stored in an array where the readings used by the processor 1604 to calculate average pressure readings. Pressure reading values (and/or average pressure values) are written out from the system at periodic intervals of a second predetermined time duration. In the example shown, pressure readings are written out every 2 ms, although this interval may vary for different embodiments. The data can be written out to an external device, such as a smartphone, laptop, pad, or other computer device using the USB port 1614, for example, or transmitted wirelessly, or outputted using other available output technology. At time intervals of a third predetermined time duration, the processor 1704 receives signals regarding motor positions from the state machine processing loop and stores this data relative to the other time data, such as pressure and, optionally, flow data. In the example shown in FIG. 17, the third predetermined time interval/duration is 10 ms, but this period can also vary with different embodiments.

Once the controller is powered on at event 1704 is starts the interrupt service routines and sets pin modes on the controller board 1602. When the control board is powered, it runs through a "Set-Up" portion of the code. This is where the interrupt service routine (ISR) is initialized, variables are initialized and input/output pins are defined. The setting of pin modes includes setting pin definitions for analog inputs (pressure sensor, control knobs of the controller 52) and digital inputs (mode switch). A cycle timer is reset to keep track of the current session and the user updates the inputs to make any changes to maximum vacuum pressure and cycle speed that may be desired, as well as to select the mode to begin processing with, which is typically, but not necessarily, the let down mode. The state machine loop is cycled at processor speed until the user decides to power off the system 100. The pumping function can be stopped without shutting off the system by selecting State 1.

Figure 18A:
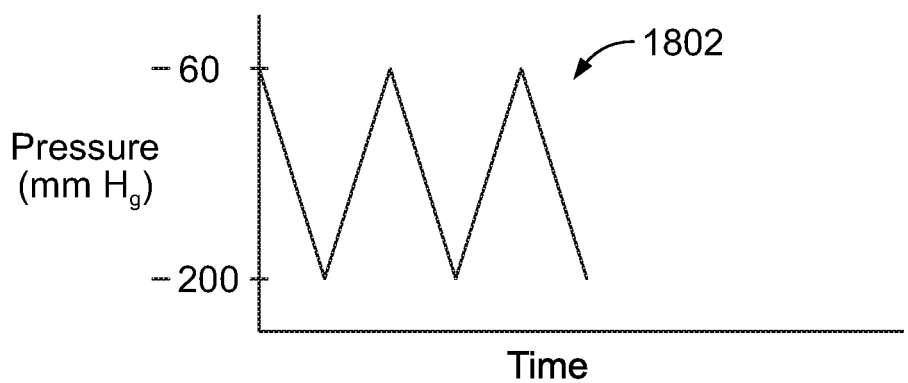
FIG. 18A shows a waveform of the pumping characteristics of the system during a let down mode, according to an embodiment of the present disclosure.

FIGS. 18A-18H illustrate pumping pressures over time for various exemplary pumping modes. It is noted that the present disclosure is not limited to the pumping modes shown, as any other pumping mode can be programmed into the controller 52 to produce any customized pumping waveform desired, within the pumping limits of the system 100. FIG. 18A shows a waveform of the pumping characteristics of the system 100 during a let down mode 1802, according to an embodiment of the present disclosure. The frequency of a let down mode is about 60 to about 150 cycles per minute, typically in a range of about 90 to 120 cycles per minute. The vacuum in the tubing is cycled between a predetermined "latch" vacuum (in the example shown, −60 mm Hg, although this may vary) and a maximum suction/vacuum (in the example shown, −200 mm hg, although this may vary). The frequency of the cycling is typically significantly higher (faster) than the frequency of a milk extraction mode. A milk extraction mode (also referred to as milk expression mode) has a typical frequency in the range of about 30 to about 90 cycles per minute. It is further noted that in regard to this mode, as well as all other modes and waveforms performed by the system 100, the frequency can be manually varied by adjustment of selector 160. Likewise, the maximum suction can be manually varied by adjustment of selector 158.

Figure 18B:
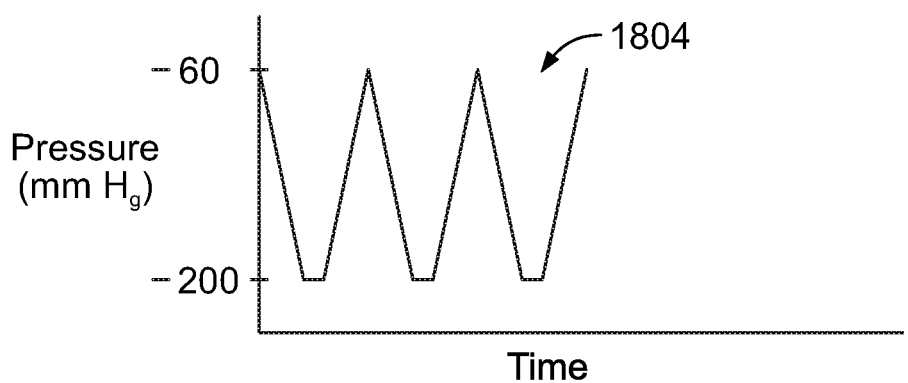
FIG. 18B shows a waveform of the pumping characteristics of the system during a let down mode, according to an alternative embodiment of the present disclosure.

FIG. 18B shows a waveform of the pumping characteristics of the system 100 during a let down mode 1804, according to an alternative embodiment of the present disclosure. The vacuum in the tubing is cycled between a predetermined "latch" vacuum (in the example shown, −60 mm Hg, although this may vary) and a maximum suction/vacuum (in the example shown, −200 mm hg, although this may vary). Upon achieving the maximum suction, the maximum suction is maintained for a predetermined time before again ramping back up to the latch pressure, during each cycle. In this embodiment, the predetermined time during which the maximum suction is maintained for each cycle is about 50% of the period of the cycle, but can be within a range of 25-75% of the period. Of course the predetermined time period can be varied to provide other embodiments of let down cycles.

Figure 18C:
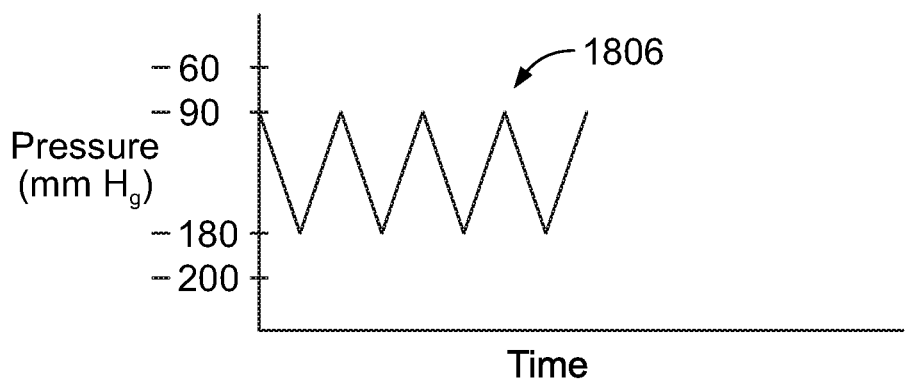
FIG. 18C shows a let down mode waveform, in which the latch pressure is lower (latch suction is higher) than in the previous embodiments, and the maximum suction is lower (pressure is lower) than in the previous embodiments.

FIG. 18C shows a let down mode waveform 1806, in which the latch pressure is lower (latch suction is higher) than in the previous embodiments, and the maximum suction is lower (pressure is lower) than in the previous embodiments. In this example, the latch pressure is −90 mm Hg and the maximum suction is −180 mm Hg. Again, FIG. 18C is for exemplary purposes only as the latch suction and maximum suction values can be programmed for many other different values.

Figure 18D:
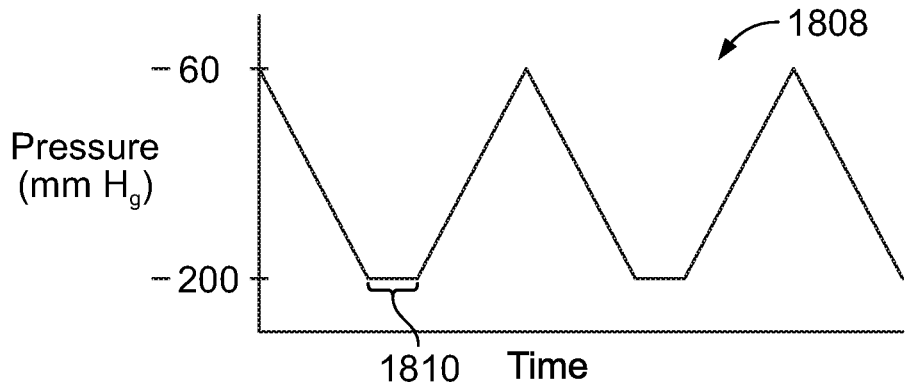
FIG. 18D shows an example of a milk extraction pumping mode according to an embodiment of the present disclosure.

FIG. 18D shows an example of a milk extraction pumping mode 1808, which is typically selected upon achieving let down, but can be selected at any time using the mode selector 156. It is notable that the milk extraction mode 1808 has a longer cycle time than the let down modes described above. Of course, other cycle times can be programmed for various other milk extraction and let down modes. Also notable is that upon achieving maximum suction, the maximum suction level is maintained for a predetermined time period 1810 with each cycle. In the example shown in FIG. 18D, the predetermined time period 1810 is about 50% of the period of the cycle, but can be within a range of 25-75% of the period. Further, the disclosure is not limited to these time periods, as shorter or longer time durations could be used. In at least one embodiment, the predetermined time period was about 10 ms, but may range, for example from about 5 ms to about 25 ms.

Figure 18E:
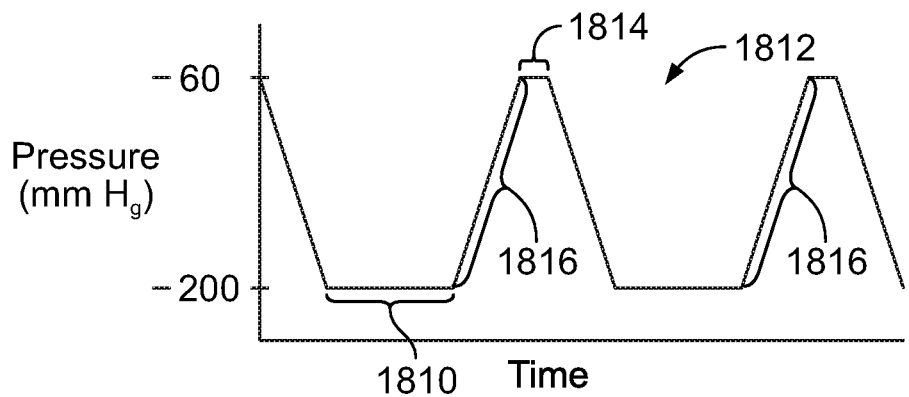
FIG. 18E shows a milk extraction waveform according to another embodiment of the present disclosure.

FIG. 18E shows another embodiment of a milk extraction waveform 1812 illustrating further customization that may be provided in the pumping characteristics of the system 100. In addition to the holding of the maximum suction for a predetermined time 1810, this mode also holds the latch suction for a predetermined time 1814 for each cycle. As shown, the predetermined time period 1814 is less than the predetermined time period 1810, but it could alternatively, be greater than or equal to 1810. Also in this embodiment, the ramp 1816 down from the maximum suction level to the latch suction level is not linear, as in the previous embodiments. This phase could follow a parabolic curve, hyperbolic curve or other nonlinear ramp curve. Further alternatively, the transition from maximum suction to latch suction could be stepped, with the pressure being maintained at one or more intermediate suction levels for one or more predetermined periods of time, with the curve between steps being linear or nonlinear, or with at least one ramp between steps being linear and at least one other ramp between steps being nonlinear. Although the transition from latch suction to maximum suction is shown in FIG. 18E as being linear, any of the modifications described above could be applied to this portion of the cycle.

Figure 18F:
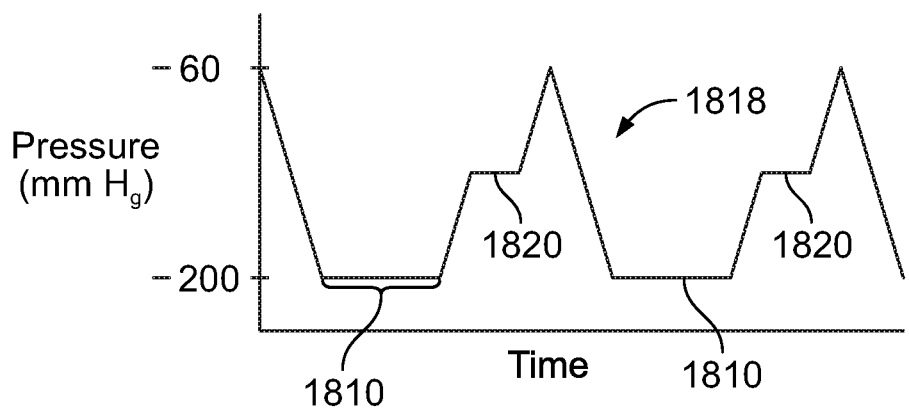
FIG. 18F illustrates an example of a waveform for a milk extraction mode in which the transition from maximum suction to latch suction is stepped, according to another embodiment of the present disclosure.

FIG. 18F illustrates an example of a waveform for a milk extraction mode in which the transition from maximum suction to latch suction is stepped, wherein step 1820 is at a suction level intermediate of the maximum suction level and the latch suction level and is maintained for a predetermined period of time before further reducing the suction (increasing the pressure) to the latch suction level.

Figure 18G:
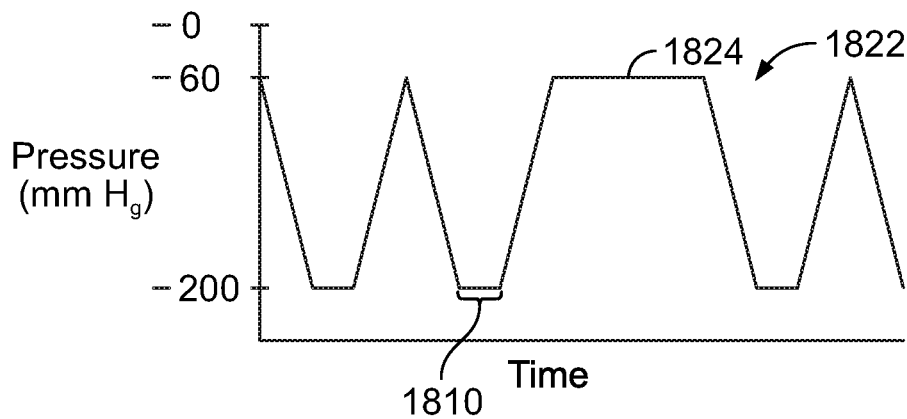
FIG. 18G illustrates an example of a milk extraction mode waveform that is programmed to pause for a predetermined period of time, according to an embodiment of the present disclosure.

FIG. 18G illustrates an example of a milk extraction mode waveform 1822 that is programmed to pause for a predetermined period of time (pause time 1824) at the latch suction level after a predetermined number of cycles or a predetermined time performing pumping cycles has elapsed. The pause time 1824 is typically much greater than time 1814 and time 1810, and is measure in seconds. For example, pause time could be from one second to several minutes, typically in a range of about thirty seconds to two minutes, typically about one to two minutes, although any time found to be beneficial could be programmed. The pause time allows the breast 2 to recover, while still maintaining attached and sealing of the breast flange 10 to the breast and maintaining vacuum in the tubing 32. The pause time may allow a time period for further let down of milk in the breast, resulting in overall higher milk expression over the same time period, compared to if the system remained pumping without any pause time. Additionally manual, self-expression can be performed during the pause time, to assist in milk removal.

Figure 18H:
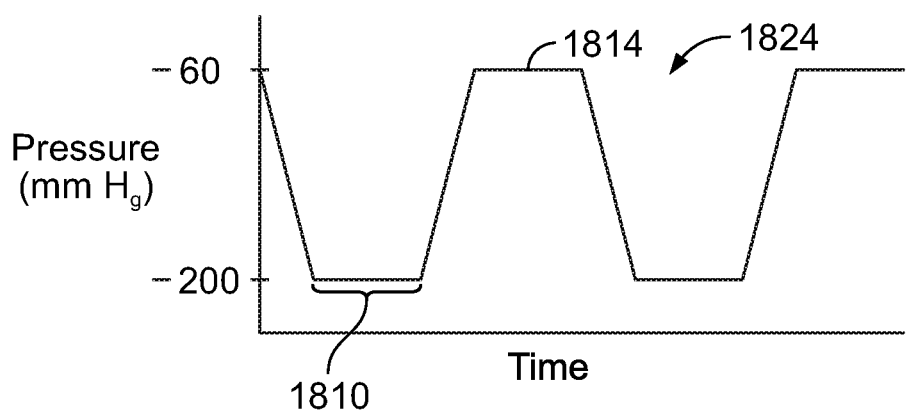
FIG. 18H illustrates a milk expression mode waveform in which both maximum suction levels and latch suction levels are maintained for predetermined time periods, according to an embodiment of the present disclosure.

FIG. 18H illustrates another example of a milk expression mode waveform in which both maximum suction levels and latch suction levels are maintained for predetermined time periods 1810, 1814 in each cycle. Time period 1814 may be less than, equal to or greater than time period 1810.

Figure 19:
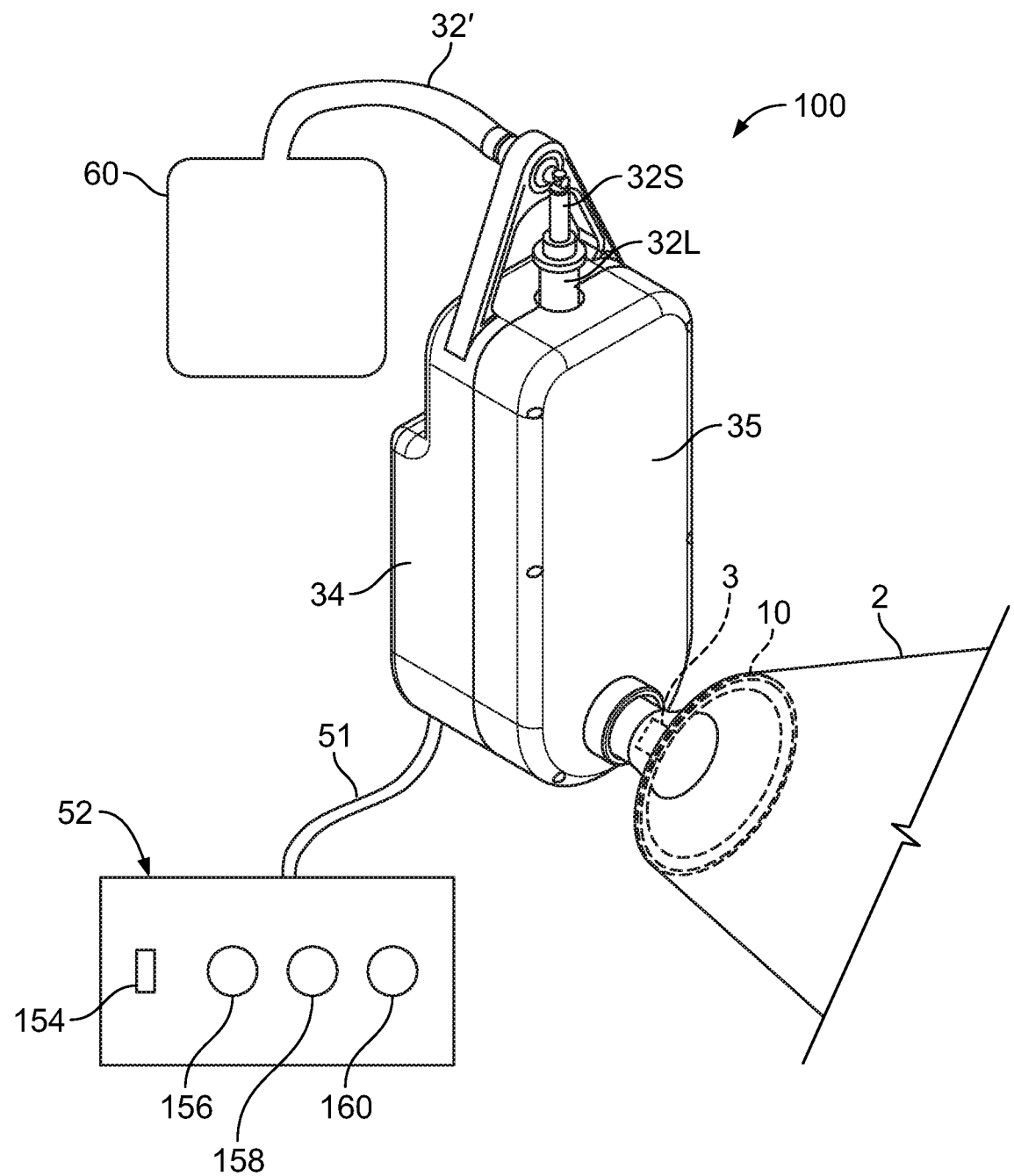
FIG. 19 is a perspective illustration of a system according to an embodiment of the present disclosure.

The compression member (e.g., pinch valve) 36 functions to lock the suction level experienced by the breast, in the vacuum chamber established within the breast flange 10 and tubing 10 distal of the compression member 36. In an exemplary user scenario, breast flange 10 is fitted over the nipple 3 of the breast 2 and held in place while the system is powered on using power switch 154, as illustrated in FIG. 19. Upon selection of a pumping mode using mode selector 156, the system 100 begins to evacuate the tubing 32 to establish suction sufficient to seal (latch) the breast flange 10 to the breast 2, after which the breast flange 10 no longer needs to be manually held in place, as the vacuum is sufficient to maintain attachment of the system 100 to the breast 2. The main body of the system 34,35 may be supported by a bra, or an immovable surface such as a table top, desk top, etc., or can be maintained in attachment with the breast via the vacuum, without any additional support. The controller 52 is typically maintained on a separate support surface, such as a table, but could be integrated within the main body 34, 35 of the system 100. The milk collection container 60 in the embodiment shown in FIG. 19 is typically externally supported by a table or other support, but could, alternatively, be mounted to and supported by the main body 34, 35.

Figure 20A:
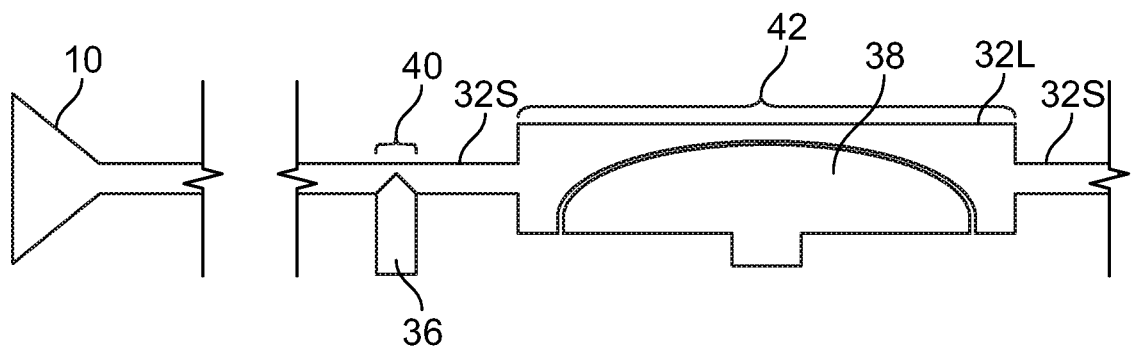
FIG. 20A illustrates preferred compression driver positions upon first placing the skin contact member in contact with the breast, prior to powering on the system, according to an embodiment of the present disclosure.

FIG. 20A illustrates the preferred compression driver 36,38 positions upon first placing the skin contact member 10 in contact with the breast 2, prior to powering on the system. Both drivers 36, 38 are in the completely compressed positions, closing off the tubing 32S, 32L in regions 40 and 42, respectively.

Upon powering up the system and selecting a latch mode, the compression member 36 opens as illustrated in FIG. 19B and the compression member 38 begins to withdraw away from anvil surface 2232 which gradually increases the suction level within tubing 32. When the predetermined maximum suction level is achieved (as confirmed by pressure readings taken from pressure sensor 54), the compression member 38 ceases its travel in the current direction, and either maintains that position for a predetermined period of time (or moves slightly in the same direction to compensate for decreasing suction as milk enters the system) when the mode has a predetermined time 1810 to maintain maximum suction, or reverses direction and compresses the tube 32L until the latch suction level is achieved. If the maximum suction level has not yet been achieved by the time that the compression member is fully retracted away from the anvil surface 2232 on the first stroke, then the compression member 36 again compresses the tube 32S to seal off the current vacuum level in the environment of the breast, and the compression member 38 fully compresses the tube portion 32L to squeeze more air out of the system (out through one-way valve 50). Then the compression member 36 reopens to fully open tube portion 32S and compression member carries out another stroke, again moving away from the anvil surface 2232 to generate a greater suction level. This cycling continues until the maximum suction level is achieved. It is noted that it is possible in some cases to achieve the maximum suction level on the first stroke, whereas in other cases, multiple strokes may be required.

Figure 20B:
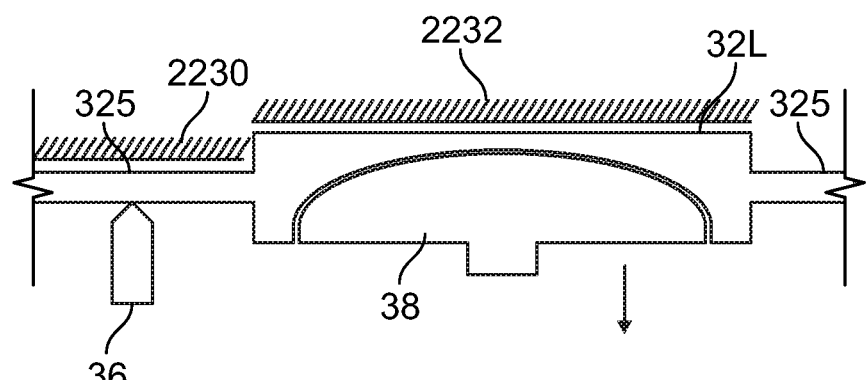
FIG. 20B shows the tubing portion fully open as the compression member is released and compression member is moving away from anvil surface to increase suction within the tubing, according to an embodiment of the present disclosure.

FIG. 20B shows the tubing portion 32S fully open as the compression member 36 is released and compression member 38 is moving away from anvil surface 2232 to increase suction within the tubing 32. Upon achieving the maximum suction, the system may be designed and programmed so that the compression member 38 does not travel to its fullest possible extent in either direction to achieve the maximum and latch suction levels, so as to allow some reserve suction and pressure producing capability. When the maximum suction level has been achieved, and the pumping profile is programmed to return to latch pressure, the compression member 38 advances toward the anvil surface 2232, compressing tubing portion 32L, thereby raising the pressure in the tubing 32. Upon achievement of the latch suction pressure, compression member 36 closes off the tubing 32S again to ensure that the latch pressure is maintained against the breast 2, so that sufficient suction is maintained. At this stage, the compression member 38 again begins moving away from the anvil surface 2232 to increase the suction level back to maximum suction, and compression member 36 opens (moves away from anvil surface 2230) to allow tube 32S to open and the breast 2 to be exposed to the maximum suction. Alternatively, the system may be programmed so that the compression member 38 cycles between maximum and latch suction levels without the compression member 36 closing during a point in each cycle, with the compression member 36 closing only when the latch pressure is exceeded.

Figure 20C:
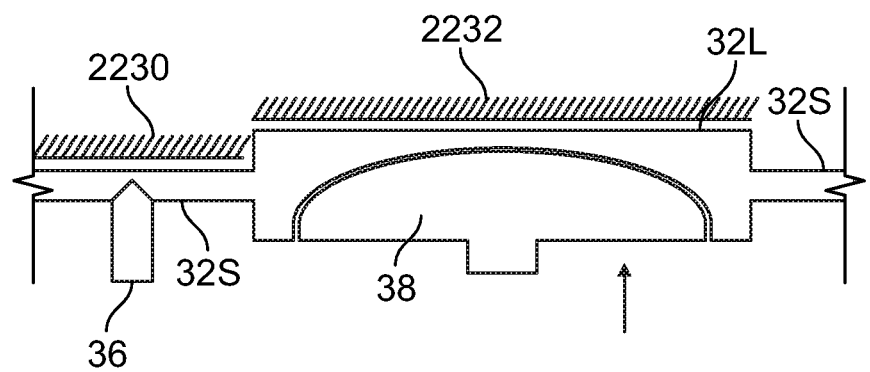
FIG. 20C shows the first compression member having sealed of the tube portion and the second compression member increasing the pressure in the tubing to establish a positive pressure to drive the contents (milk) out through a one-way valve, according to an embodiment of the present disclosure.

Upon selection of a milk extraction mode, the compression member 36 and compression member 38 function in the same manners as in the latch mode, but in a manner that follows an extraction waveform determined by the selected extraction mode. During the compression stroke of compression member 38, compression member 36 closes when the latch pressure/suction level is achieved. Continued compression by the compression member 38 (FIG. 20C) increases the pressure in the tubing 32 downstream of the compression member 36 to establish a positive pressure to drive the contents (milk) of tube portion 32L out of the tube portion 32L through smaller tubing portion 32S downstream of 32L and out through one-way valve 50. The positive pressure attained is sufficient to open the one-way valve for delivery of the milk out of the tubing 32 and into the milk collection container 60. In one embodiment, the positive pressure is in the range of 20 mm Hg to 40 mm Hg, typically about 25 mm Hg. Upon reversing the motion of compression member 38, compression member 36 opens when the suction level returns to the latch suction level and compression member 38 continues to open to increase the suction level to the maximum suction level.

The system 100 is responsive to pressure changes within the tubing 32 caused by entry of milk into the tubing. As milk enters the system, the suction level decreases (pressure increases). The feedback provided by pressure monitoring via pressure sensor 54 provide input to a feedback loop that adjusts the position of the compression member 38 to maintain the desired vacuum (pressure) within the tubing by compensating for the changes in pressure that occur to changing amounts of milk in the tubing 32. For example, for a relatively larger amount of milk in the tubing, this will require a relatively shorter stroke of the compression member 38 toward anvil surface 2232 to achieve the latch pressure. This modification can be addressed by either slowing the movements of the compression member 38 to achieve the same timing cycle for pumping, or increasing the cycle frequency due to the less time taken for the shorter strokes of the compression member 38.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure as described herein.

That which is claimed is:

1. An automated system for controlling pumping cycles to pump milk from a breast, the automated system comprising:
   a breast adapter configured and dimensioned to form a seal with the breast;
   a housing;
   a storage container for storing the milk pumped from the breast;
   a conduit in fluid communication and interconnecting with the breast adapter and the storage container, the conduit having a first portion with a first inner diameter and a second portion with a second inner diameter greater than the first inner diameter and extending upwardly within the housing thereby providing an upward path for the milk within the housing from the breast adapter to the storage container; and a first compression member configured to compress the first portion of the conduit; a second compression member configured to compress the second portion of the conduit; wherein the first portion has a first compliance and the second portion has a second compliance different than the first compliance and wherein the second compression member applies a longer stroke for generating a greater vacuum than if the first inner diameter equaled the second inner diameter and for finer control of vacuum level variation.

2. The automated system of claim 1, further comprising a driving mechanism configured to compress the first portion of the conduit or the second portion of the conduit.

3. The automated system of claim 2, wherein the driving mechanism comprises a roller paddle configured to roll against the conduit.

4. The automated system of claim 1, wherein at least a latch suction is maintained throughout a pumping session.

5. The automated system of claim 4, wherein the latch suction applied to the breast for expression of the milk comprises a first suction level, and wherein, during expulsing, a second suction level is maintained against the breast, the second suction level being lower than the first suction level.

6. The automated system of claim 1, further comprising a controller configured to control operational settings of the automated system.

7. The automated system of claim 1, wherein the first portion of the conduit has a first hardness which differs from a second hardness of the second portion of the conduit.

8. The automated system of claim 1, further comprising a flange adapter, wherein the flange adapter is removable from the automated system.

9. The automated system of claim 1, further comprising a pressure sensor configured to sense pressure between the breast and the breast adapter.

10. The automated system of claim 1, wherein the conduit is reinforced with ribs.

11. The automated system of claim 1, wherein the automated system provides a plurality of pumping waveform patterns.

12. The automated system of claim 1, further including a sensor, the sensor sensing one or more of flow, temperature, proximity, motion or other sensor capable of providing information usable to monitor the safety or function of a pump mechanism of the automated system.

13. The automated system of claim 1, wherein a one or more sensor can be positioned at the breast, proximal or distal to a pumping structure, or proximal or distal to a valve.

14. The automated system of claim 1, wherein a controller adaptively controls movement of the first compression member and the second compression member with input from a feedback loop established with a pressure sensor.

* * * * *